(12) United States Patent
Casares Lagar et al.

(10) Patent No.: US 8,524,860 B2
(45) Date of Patent: Sep. 3, 2013

(54) PEPTIDES WITH CAPACITY TO BIND TO SCURFIN AND APPLICATIONS

(75) Inventors: Inés Noelia Casares Lagar, Pamplona (ES); Francisco Borrás Cuesta, Pamplona (ES); Pablo Sarobe Ugarriza, Pamplona (ES); Jesús Maria Prieto Valtueña, Pamplona (ES); Juan José Lasarte Sagastibelza, Pamplona (ES)

(73) Assignee: Proyecto de Biomedicina CIMA, S.L., Navarra (ES)

( * ) Notice: Subject to any disclaimer, the term of this patent is extended or adjusted under 35 U.S.C. 154(b) by 0 days.

(21) Appl. No.: 12/743,616

(22) PCT Filed: Nov. 14, 2008

(86) PCT No.: PCT/ES2008/000716
§ 371 (c)(1),
(2), (4) Date: May 19, 2010

(87) PCT Pub. No.: WO2009/065982
PCT Pub. Date: May 28, 2009

(65) Prior Publication Data
US 2010/0267623 A1    Oct. 21, 2010

(30) Foreign Application Priority Data
Nov. 19, 2007 (ES) .................................. 200703052

(51) Int. Cl.
*C07K 2/00* (2006.01)

(52) U.S. Cl.
USPC ........................................ 530/300; 424/193.1

(58) Field of Classification Search
None
See application file for complete search history.

(56) References Cited

U.S. PATENT DOCUMENTS

| | | | |
|---|---|---|---|
| 5,922,245 A * | 7/1999 | Mohri et al. | 252/512 |
| 6,221,355 B1 * | 4/2001 | Dowdy | 424/192.1 |
| 6,414,129 B1 | 7/2002 | Brunkow et al. | |

FOREIGN PATENT DOCUMENTS

| | | |
|---|---|---|
| WO | 02/090600 A2 | 11/2002 |
| WO | 2006/044864 A2 | 4/2006 |
| WO | 2007/084775 A2 | 7/2007 |

OTHER PUBLICATIONS

Ngo et al., 1994, The Protein Folding Problem and Tertiary Structure Prediction, pp. 492-495.*
Belkaid, Eur. J. Imm. 2008, vol. 39, p. 918-921.*
Casares, Noelia, et al., "CD4+/CD25+ Regulatory Cells Inhibit Activation of Tumor-Primed CD4+ T Cells with IFN-v-Dependent Antiangiogenic Activity, as well as Long-Lasting Tumor Immunity Elicited by Peptide Vaccination," The Journal of Immunology, 2003, pp. 5931-5939, vol. 171, No. 11, The American Association of Immunologists, Inc., Pamplona, Spain.
Yagi, Haruhiko, et al., "Crucial role of FOXP3 in the development and function of human CD25+CD4+ regulatory T cells," International Immunology, 2004, pp. 1643-1656, vol. 16, No. 11, The Japanese Society for Immunology.
Zuo, Tao, et al., "FOXP3 is an X-linked breast cancer suppressor gene and an important repressor of the HER-2/ ErbB2 oncogene," Cell, 2007, pp. 1275-1286, vol. 129, No. 7, National Institutes of Health.

* cited by examiner

*Primary Examiner* — Yunsoo Kim
(74) *Attorney, Agent, or Firm* — Tristan A. Fuierer; Andrew D. Gerschutz; Moore & Van Allen, PLLC

(57) ABSTRACT

The invention relates to peptides of general formula (I), wherein X is absent or X is present and is $X_{14}$ or $X_{14}$-$X_{15}$, wherein $X_{14}$ and $X_{15}$, independently from one another, represent an amino acid; their functional variants and fragments, and their pharmaceutically acceptable salts, having the capacity to bind to scurfin and inhibit its biological activity, therefore they regulate or block the activity of regulatory T (Treg) lymphocytes. They are applicable in the treatment of infectious and neoplastic diseases.

(I)
Arg-Asp-Phe-Gln-Ser-Phe-Arg-Lys-Met-Trp-Pro-Phe-Phe-X

16 Claims, 10 Drawing Sheets

PEPTIDES WITH CAPACITY TO BIND TO SCURFIN AND APPLICATIONS

CROSS-REFERENCE TO RELATED APPLICATIONS

This application is filed under the provisions of 35 U.S.C. §371 and claims the priority of International Patent Application No. PCT/ES2008/000716 filed on 14 Nov. 2008 entitled "Peptides with Capacity to Bind to Scurfin and Applications" in the name of Ines Noelia Casares Lagar, et al., which claims priority of Spanish Patent Application No. P200703052 filed on 19 Nov. 2007, both of which are hereby incorporated by reference herein in their entirety.

FIELD OF THE INVENTION

The invention generally relates to peptides having the capacity to bind to scurfin and to their applications. The invention particularly relates to peptides inhibiting the biological activity of scurfin by means of their direct binding to said protein and which thus allow regulating or blocking the activity of regulatory T (Treg) lymphocytes. Said peptides can be used in the treatment of pathologies in which it is suitable or necessary to regulate or block the activity of Treg lymphocytes in a controlled manner, such as infectious and neoplastic diseases.

BACKGROUND OF THE INVENTION

At the beginning of the 1970s, the presence of T lymphocytes capable of suppressing immune responses was described for the first time. At that time, it was believed that said suppressive action was mediated by a specific cell subpopulation, but no specific marker of said subpopulation was managed to be cloned or characterized and the interest for this cell subtype was partly lost. However, in 1995, Sakaguchi et. al. (Sakaguchi et al. 1995. J Immunol 155:1151-64) discovered that a minority population of CD4+ cells (10%) which co-expressed the interleukin 2 receptor alpha chain (CD25) was crucial for controlling autoreactive cells and autoimmunity in vivo. Since then, many groups have demonstrated that this subpopulation of CD4+CD25+ cells, also known as Treg lymphocytes or Treg cells, are immunosuppressive (Takahashi et al. 1998. Int Immunol 10:1969-80; Thornton & Shevach. 1998. J Exp Med 188:287-96). These cells were first identified in mice but have later been extensively characterized in humans (Dieckmann et al. 2001. J Exp Med 193:1303-10; Jonuleit et al. 2001. J Exp Med 193:1285-94; Levings et al. 2001. J Exp Med 193:1295-302). The existence of a specific immunosuppressive subpopulation is currently widely accepted by the scientific community and the way to manipulate its activity for its clinical use is sought. The main issue is how its activity could be modulated.

Treg lymphocytes are essential for the protection against autoimmune diseases and for the prevention of rejection to transplants; therefore, the posibility of enhancing their activity has a great potential in the treatment of the autoimmune diseases and in organ transplants. However, due to the fact that tumors express autoantigens, Treg lymphocytes can be capable of inhibiting the activation of immune responses against cancer.

Several groups, including the group of the inventors, have demonstrated that the simple elimination of CD4+CD25+ (Treg) cells by the in vivo administration depleting antibodies facilitates the induction of antitumor immunity and the protection against cancer development (Casares et al. 2003. J Immunol 171:5931-9; Onizuka et al. 1999. Cancer Res 59:3128-33; Shimizu et al. 1999. J Immunol 163:5211-8; Steitz et al. 2001. Cancer Res 61:8643-6; Sutmuller et al. 2001. J Exp Med 194:823-32). It is thus believed that CD4+CD25+ (Treg) cells are continuously slowing down the activation of effector T lymphocytes to prevent autoimmunity processes, but at the same time making the correct activation of an antitumor response difficult when it is necessary.

Immunotherapy is very promising for the treatment of patients with cancer. The numerous clinical protocols carried out which have used therapies based on cytokines, infusions of effector T cells or vaccination protocols have demonstrated that cancer immunotherapy is generally safe. However, although the induction of immune responses after the treatments has been observed in these clinical protocols, most of the patients are incapable of developing an effective antitumor response. A meta-analysis of 37 independent clinical vaccination protocols including more than 700 patients has showed that the percentage of partial or complete responses against the tumor is very low (3.8%) (Rosenberg et al. 2004. Nat Med 10:909-15). The recent demonstration of the presence of Treg lymphocytes in the tumor tissue or the lymph nodes of patients with melanoma (Wang, H. Y., J Immunol, 2005. 174:2661-2670; Viguier, M., F. J Immunol, 2004. 173: 1444-1453), lung cancer (Woo, E. Y., Cancer Res 61:4766-4772), ovarian cancer (Woo, E. Y., Cancer Res, 2001. 61:4766-4772, Curiel, T. J., Nat Med, 2004. 10:942-949), pancreatic cancer and breast cancer (Liyanage, U. K., J Immunol, 2002. 169:2756-2761) as well as in hepatocarcinomas (Ormandy, L. A. Cancer Res, 2005. 65:2457-2464; Kobayashi, N., Clin Cancer Res, 2007. 13:902-911) and the description that tumor tissue secretes chemokines which specifically attract this subpopulation towards tumor tissue indicate that the access of Treg lymphocytes to the tumor is a dynamic process and that it exerts an immunosuppressive effect facilitating the progression of the disease. The presence of Treg in the tumor as well as in peripheral nodes could explain the low efficacy of the immunotherapy protocols. In the same way, in infectious diseases, the control exerted by Treg lymphocytes can limit the magnitude of the effector T responses and cause the failure in the control of the infection. It has thus been described that some viruses such as hepatitis B virus (Xu, D. J Immunol, 2006. 177:739-747), hepatitis C virus (Boettler, T., J Virol, 2005. 79:7860-7867; Cabrera, R. Hepatology, 2004. 40:1062-1071; Rushbrook, J Virol, 2005. 79:7852-7859; Sugimoto, K. Hepatology, 2003. 38:1437-1448) and HIV, (Aandahl, E. M. J Virol, 2004. 78:2454-2459; Kinter, A. L. J Exp Med, 2004. 200:331-343; Oswald-Richter, K. PLoS Biol 2004. 2:E198; Weiss, L. Blood, 2004. 104: 3249-3256) can use Treg lymphocytes to block the antiviral immune response and thus allow the establishment of the persistent chronic infection. Due to all this, it is believed that the modulation of the action of Treg lymphocytes can be essential in the development of immunotherapies against cancer or against infectious diseases.

There is a certain controversy with regard the mode of action of Treg lymphocytes, but the role of cytokine TGF-β (transforming growth factor-β) in the process for inhibiting effector T cells seems to be increasingly coherent (Powrie et al. 1996. J Exp Med 183:2669-74; Somasundaram et al. 2002. Cancer Res 62:5267-72).

In addition, it has recently been described that the transcription factor scurfin (FOXP3, expression product of the foxp3 gene) (Yagi et al. 2004. Int Immunol 16:1643-56. 2004 Oct. 4) is essential for the activity of Treg lymphocytes, such that its presence determines the suppressive activity of these cells. The cDNA sequences encoding murine and human scurfin have been the object of U.S. Pat. No. 6,414,129 which furthermore describes that the modulation of the expression of scurfin can have therapeutic effects in various diseases; said patent also mentions the use of synthetic peptides, among other molecules, to regulate the expression of the foxp3 gene but does not mention anything about the possibility of inhibiting the activity of the already expressed scurfin.

Likewise, the use of a method for enhancing the immune response in mammals based on the elimination of Treg lymphocytes by means of using neutralizing monoclonal antibodies (WO 2006/044864); however, said patent application does not mention anything about the transient regulation of the activity of Treg lymphocytes by means of inhibiting the activity of scurfin (essential in the immunosuppressive effect of said cells). In addition, the depletion of Treg lymphocytes increases the risk of induction of autoimmunity and the fact that such monoclonal antibodies do not discriminate between Treg lymphocytes and effector T lymphocytes reduces their application.

Currently, the only methods for inhibiting the activity of Treg lymphocytes which have been experimentally described involve their elimination, by means of using depleting antibodies or by means of blocking the cytokines that they produce and which may be responsible for their activities (TGF-β, IL-10), but there is no specific inhibitor of this cell subpopulation. The methods which are based on the depletion of the regulatory T cells have the drawback that they eliminate the cells and involve risks of causing autoimmune diseases. Furthermore, there are no specific antibodies for regulatory T cells and those that exist can also eliminate effector T cells.

It is therefore still necessary to identify new compounds capable of regulating or blocking the activity of Treg lymphocytes, potentially useful in human therapy.

SUMMARY OF THE INVENTION

It has now surprisingly been discovered that the immunosuppressive activity of Treg lymphocytes can be transiently or temporarily regulated or blocked by inhibiting the activity of scurfin, an essential transcription factor for said Treg lymphocytes to exert their immunosuppressive effect, by means of using peptides not only capable of binding to scurfin but also capable of inhibiting its biological activity. Said peptides with capacity to bind to scurfin, particularly those peptides capable of inhibiting its biological activity, are potentially useful for the treatment of pathologies requiring a transient or temporary regulation or inhibition of the immunosuppressive activity of Treg lymphocytes, such as infectious diseases and neoplastic diseases. Said peptides likewise provide a tool for studying the biological role of scurfin and Treg lymphocytes.

Therefore, one aspect of this invention relates to peptides having the capacity to bind to scurfin. In a particular and preferred embodiment, said peptides further have the capacity to inhibit the biological activity of scurfin.

In another aspect, the invention relates to a fusion protein comprising a peptide provided by this invention and a carrier peptide with capacity to internalize a peptide in a cell.

In another aspect, the invention relates to a pharmaceutical composition comprising at least one peptide or one fusion protein provided by this invention.

In another aspect, the invention relates to the use of said peptides and fusion proteins in the preparation of a medicinal product for the treatment of a pathology requiring a transient regulation or inhibition of the immunosuppressive activity of Treg lymphocytes, such as a neoplastic disease or an infectious disease.

In another aspect, the invention relates to the use of said peptides and fusion proteins in the treatment of a pathology requiring a transient regulation or inhibition of the immunosuppressive activity of Treg lymphocytes, such as a neoplastic disease or an infectious disease.

In another aspect, the invention relates to nucleic acids encoding said peptides or said fusion proteins.

In another aspect, the invention relates to a gene construct comprising a nucleic acid encoding a peptide or a fusion protein provided by this invention.

In another aspect, the invention relates to a vector comprising said nucleic acid or said gene construct.

In another aspect, the invention relates to a host cell, such as a transformed host cell, comprising said nucleic acid, said gene construct or said vector.

In another aspect, the invention relates to a process for producing a peptide or a fusion protein provided by this invention comprising culturing said host cells under conditions allowing the expression of said peptide and, if desired, recovering the peptide or the fusion protein obtained.

In another aspect, the invention relates to the use of said nucleic acids and gene constructs in the preparation of vectors and cells for the treatment of a pathology requiring a transient regulation or inhibition of the immunosuppressive activity of Treg lymphocytes, such as a neoplastic disease or an infectious disease.

BRIEF DESCRIPTION OF THE DRAWINGS

FIG. 10A shows the average tumor growth in different groups of BALB/c mice inoculated subcutaneously with $5 \times 10^5$ tumor cells (CT26). The different groups represent the average tumor evolution in the absence of treatment (Control group, white triangle), treated with vaccine antigen AH1 alone (black triangle), treated with peptide P60 alone (SEQ ID NO: 1) (white circle) or treated with the vaccine antigen in combination with peptide P60 (SEQ ID NO: 1) (black circle). FIG. 10B shows the survival curves of the different experimental groups (Kaplan-Meier Representation). p<0.001 indicates the result of the statistical analysis by means of the log-rank test.

DETAILED DESCRIPTION OF THE INVENTION

Peptide of the Invention

Figure 1:
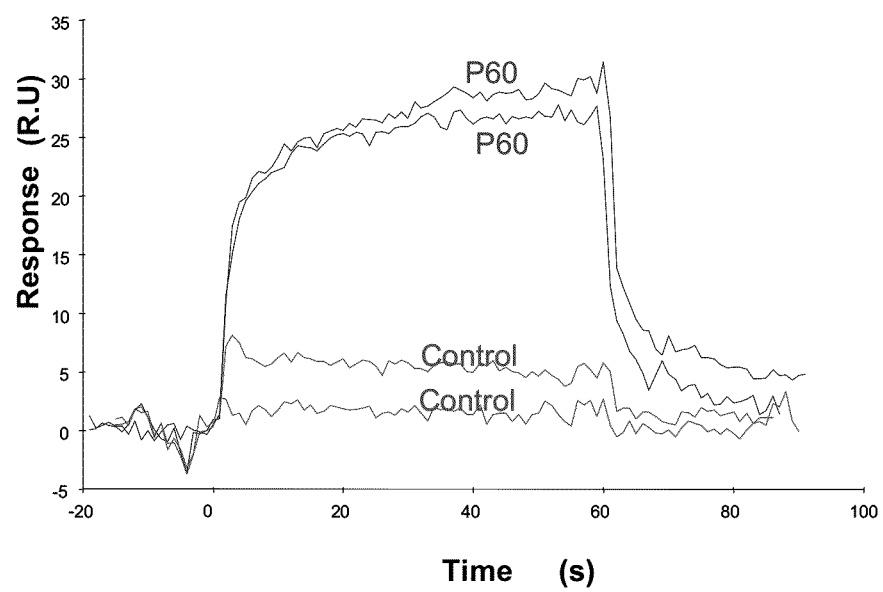
FIG. 1 is a graph showing the results of a surface plasmon resonance (SPR) analysis of the biomolecular interaction occurring between peptide P60 (SEQ ID NO: 1) and scurfin, as it is described in Example 1 (section 1.3). As can be seen, peptide P60 (SEQ ID NO: 1) gives a positive signal proving its capacity to bind specifically to scurfin. The result shown is representative of 3 independent experiments. R.U.: relative units.

In one aspect, the invention relates to a peptide, hereinafter peptide of the invention, with capacity to bind to scurfin, selected from:

a) a peptide of general formula (I) comprising the amino acid sequence:

$$\text{Arg-Asp-Phe-Gln-Ser-Phe-Arg-Lys-Met-Trp-Pro-Phe-Phe-X} \quad (I)$$

wherein
X is absent or X is present and is $X_{14}$ or $X_{14}$-$X_{15}$, wherein
$X_{14}$ and $X_{15}$, independently from one another, represent an amino acid;
b) a variant of the peptide defined in a); and
c) a fragment of the peptide defined in a) or of a variant defined in b); and its pharmaceutically acceptable salts.

The term "peptide", as used herein, relates to a polymer formed by the binding, in a defined order, of alpha-amino acids by means of a peptide bond, and includes modifications or derivatives thereof, for example, glycosylation, phosphorylation, acetylation, amidation, etc.

The amino acids of the peptide of the invention, depending on the orientation of the amino group of the alpha carbon atom can belong to the L series or to the D series, preferably to the L series.

The amino acids represented by $X_{14}$ and $X_{15}$ can be natural amino acids or modified or uncommon amino acids. Natural amino acids include aliphatic amino acids (glycine, alanine, valine, leucine and isoleucine), hydroxylated amino acids (serine and threonine), sulfured amino acids (Cysteine and methionine), dicarboxylic amino acids and their amides (aspartic acid, asparagine, glutamic acid and glutamine), amino acids having two basic groups (lysine, arginine and histidine), aromatic amino acids (phenylalanine, tyrosine and tryptophan) and cyclic amino acids (proline). Illustrative non-limiting examples of modified or uncommon amino acids include 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, 6-N-methyl-lysine, N-methylvaline, norvaline, norleucine, ornithine, etc.

The peptide of the invention is characterized by its capacity to bind to scurfin, and advantageously, by its capacity to inhibit the biological activity of scurfin. The capacity of a peptide to bind to scurfin can be determined by means of any suitable methods which allows determining the binding between two molecules (e.g., by means of an affinity assay), said method comprising putting scurfin in contact with the peptide to be assayed under conditions allowing the binding of said peptide to scurfin and evaluating the binding between the peptide and scurfin. In a particular embodiment, said affinity assay can be carried out using the surface plasmon resonance (SPR) technique (Example 1.3) or similar techniques using radioactively labeled scurfin, or, alternatively, radioactively labeling the peptide to be assayed. This type of affinity assay generally comprises putting scurfin, e.g., immobilized in the wells of a plate, in contact with the peptide the capacity to bind to scurfin of which is to be known, and, after incubating for a suitable time period, analyzing the binding of the peptide to scurfin. The peptides with low affinity for scurfin are eliminated by means of washings whereas the peptides with higher affinity remain bound to scurfin and can be released by breaking the molecular interactions between both molecules, which can be carried out by lowering the pH, for example.

The peptide of the invention is advantageously characterized not only by its capacity to bind to scurfin but also by its capacity to inhibit the biological activity of scurfin and, as a result, indirectly regulate or block, transiently or temporarily, the immunosuppressive activity of Treg lymphocytes. Although, there is no intention to be bound by any theory, it is believed that the capacity of a peptide to inhibit the biological activity of scurfin is due to the direct binding of said peptide to scurfin. The capacity of a peptide to inhibit the biological activity of scurfin can be analyzed, in vitro, by any suitable method illustrating such effect, e.g.:

a) by means of an assay based on measuring the cell proliferation in a culture of effector T lymphocytes, in the presence of an anti-CD3 antibody, Treg lymphocytes and tritiated thymidine, and in the presence or absence of the peptide to be assayed; or b) by means of an assay based on co-culturing splenocytes from OT-1 transgenic mice (mice in which T lymphocytes have a specific T cell receptor for the peptide SIINFEKL (SEQ ID NO: 7) of ovalbumin) with Treg lymphocytes in the presence of antigen [peptide SIINFEKL (SEQ ID NO: 7)], in the presence or absence of Treg lymphocytes, and in the presence or absence of the peptide to be assayed; or, alternatively c) by means of an assay based on a mixed lymphocyte reaction (MLR) in which effector cells from a mouse (e.g., BALB/c) are mixed with dendritic cells obtained from another mouse strain (e.g., C57BL/6) in the presence or in the absence of Treg lymphocytes obtained from a mouse of one of the strains (e.g., BALB/c) and in the presence or absence of the peptide to be assayed.

Similarly, similar experiments can be carried out using Treg lymphocytes of human origin. Example 3 describes in detail different assays aimed at evaluating the capacity of the peptide to be assayed (e.g., a peptide of the invention) to inhibit the biological activity of scurfin in vitro.

In a particular embodiment, the peptide of the invention is a peptide of general formula (I) comprising the amino acid sequence:

Arg-Asp-Phe-Gln-Ser-Phe-Arg-Lys-Met-Trp-Pro-Phe-Phe-X wherein X has the meaning previously indicated in relation to formula (I).

In another particular embodiment, the peptide of the invention is a peptide of general formula (Ia) [peptide of formula (I) wherein X is $X_{14}$-$X_{15}$] and comprises or is formed by the amino acid sequence:

(Ia)
Arg-Asp-Phe-Gln-Ser-Phe-Arg-Lys-Met-Trp-Pro-Phe-Phe-$X_{14}$-$X_{15}$ wherein $X_{14}$ and $X_{15}$, independently from one another, represent a natural amino acid (e.g., Gly, Ala, Val, Leu, Ile, Ser, Thr, Cys, Met, Asp, Asn, Glu, Gln, Lys, Arg, His, Phe, Tyr, Trp or Pro) or a modified or uncommon amino acid (e.g., Aad, bAad, bAla, Abu, 4Abu, Acp, Ahe, Aib, bAib, Apm, Dbu, Des, Dpm, Dpr, EtGly, EtAsn, Hyl, aHyl, 3Hyp, 4Hyp, Ide, aIle, MeGly, MeIle, MeLys, MeVal, Nva, Nle or Orn). Although $X_{14}$ and $X_{15}$ can be identical or different, in a specific embodiment, $X_{14}$ and $X_{15}$ are different, for example, $X_{14}$ is Ala and $X_{15}$ is Met.

In another particular and preferred embodiment, the peptide of the invention is a peptide comprising or formed by the amino acid sequence:

```
                                                    (SEQ ID NO: 1)
Arg-Asp-Phe-Gln-Ser-Phe-Arg-Lys-Met-Trp-Pro-Phe-

Phe-Ala-Met
```

The peptide formed by SEQ ID NO: 1 is occasionally identified in this description as peptide P60.

In another particular embodiment, the peptide of the invention is a peptide of general formula (Ib) [peptide of formula (I) wherein X is $X_{14}$] and comprises or is formed by the amino acid sequence:

```
                                                    (Ib)
Arg-Asp-Phe-Gln-Ser-Phe-Arg-Lys-Met-Trp-Pro-Phe-

Phe-X
``` wherein X is $X_{14}$, wherein $X_{14}$ represents a natural amino acid such as Gly, Ala, Val, Leu, Ile, Ser, Thr, Cys, Met, Asp, Asn, Glu, Gln, Lys, Arg, His, Phe, Tyr, Trp or Pro, or a modified or uncommon amino acid (e.g., Aad, bAad, bAla, Abu, 4Abu, Acp, Ahe, Aib, bAib, Apm, Dbu, Des, Dpm, Dpr, EtGly, EtAsn, Hyl, aHyl, 3Hyp, 4Hyp, Ide, aIle, MeGly, MeIle, MeLys, MeVal, Nva, Nle u Orn), preferably Ala.

In another particular embodiment, the peptide of the invention is a peptide comprising or formed by the amino acid sequence:

```
                                                    (SEQ ID NO: 3)
Arg-Asp-Phe-Gln-Ser-Phe-Arg-Lys-Met-Trp-Pro-Phe-

Phe-Ala
```

In another particular embodiment, the peptide of the invention is a peptide of general formula (Ic) [peptide of formula (I) wherein X is absent] and comprises or is formed by the amino acid sequence:

```
                                                    (Ic)
Arg-Asp-Phe-Gln-Ser-Phe-Arg-Lys-Met-Trp-Pro-Phe
```

In another particular embodiment, the peptide of the invention is a peptide formed by the amino acid sequence:

```
                                                    (SEQ ID NO: 2)
Arg-Asp-Phe-Gln-Ser-Phe-Arg-Lys-Met-Trp-Pro-Phe-Phe
```

Figure 2:
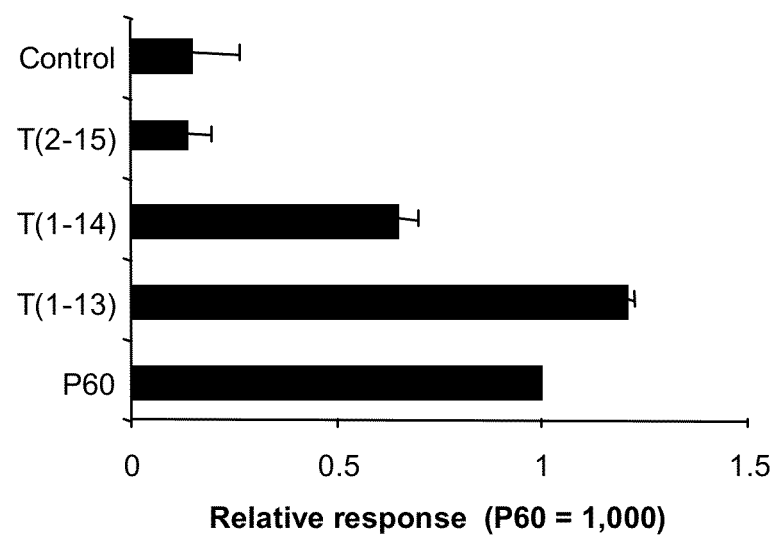
FIG. 2 is a graph showing the results of a surface plasmon resonance (SPR) analysis of the biomolecular interaction occurring between peptide P60 (SEQ ID NO: 1) and its truncated forms T(1-13) SEQ ID NO: 2, T(1-14) (SEQ ID NO: 3) and T(2-15) (SEQ ID NO: 4), and scurfin (Example 1, section 1.4). As can be seen, the elimination of an amino acid in an amino-terminal position inhibits the capacity of the peptide to bind to scurfin; however, the elimination of residues 14 or 15 of the carboxyl-terminal end does not destroy the capacity of the peptide to bind to scurfin.

Assays conducted by the inventors have shown the important role carried out by the amino-terminal end of the peptide of general formula (I) in the capacity of the peptide to bind to scurfin since the elimination of the amino acid of the amino-terminal end (Arg) drastically reduces the capacity of the peptide to bind to scurfin, whereas the elimination of residues 14 or 15 of the carboxyl-terminal end, i.e., of moiety "X", does not affect the capacity of the peptide to bind to scurfin (Example 1.4, FIG. 2).

In another particular embodiment, the peptide of the invention is a variant of the peptide of general formula (I) defined in section a). The term "variant", as used herein, relates to a peptide substantially homologous and functionally equivalent to the peptide of general formula (I) defined in section a). As used herein, a peptide is "substantially homologous" to another peptide when its amino acid sequence has a degree of identity of at least 50%, advantageously of at least 60%, preferably of at least 70%, more preferably of at least 80%, still more preferably of at least 90%, and even more preferably of at least 95%. Likewise, the expression "functionally equivalent", as used herein, means that the peptide in question (variant) maintains the capacity to bind to scurfin and, advantageously, to inhibit, in vitro and/or in vivo, the biological activity of scurfin. The capacity of a peptide to bind to scurfin can be determined by any suitable conventional method, as has been previously mentioned, for example, by means of an affinity assay, such as an affinity assay based on the surface plasmon resonance (SPR) technique (Example 1.3). Likewise, the capacity of a peptide to inhibit the biological activity of scurfin can be determined by any suitable conventional method, as has been previously mentioned, for example, by means of any of the assays described in Example 3. In a particular embodiment, the peptide of the invention is a variant having one or more insertions, deletions and/or modifications of one or more amino acids of the amino acid sequence shown in section a), and maintains the capacity to bind to scurfin. In a specific embodiment, said variant comprises one or more conservative substitutions of amino acids, with respect to the previously mentioned amino acid sequence.

In another particular embodiment, the peptide of the invention is a fragment of the peptide of general formula (I) defined in section a) or of the variant defined in section b). The term "fragment", as used in the present description, relates to a peptide comprising a portion of at least 5 consecutive amino acids of the peptide of general formula (I) defined in section a), or of the variant defined in section b), i.e., a sequence of at least 5 contiguous amino acids comprised within the amino acid sequence of general formula (I) mentioned in said section a), or of the variant defined in section b), maintaining the capacity to bind to scurfin. In a particular embodiment, the peptide of the invention is a fragment of the peptide of general formula (I) defined in a), or of the variant defined in b), comprising 5 or more (i.e., 6, 7, 8, 9, 10, 11, 12, 13 14 or 15) contiguous amino acids of the amino acid sequence of general formula (I) mentioned in section a), or of the variant defined in section b), in which one or more amino acids have been eliminated from the amino-terminal end or from the carboxyl-terminal end, or from both ends, maintaining the capacity to bind to scurfin, and, advantageously, the capacity to inhibit the biological activity of scurfin. The capacity of a peptide fragment to bind to scurfin can be determined by any suitable conventional method, as has been previously mentioned, for example, by means of an affinity assay, such as an affinity assay based on the SPR technique (Example 1.3). Similarly, the capacity of a peptide fragment to inhibit the biological activity of scurfin can be determined by any suitable conventional method, as has been previously mentioned, such as, for example, by means of any of the assays described in Example 3.

Likewise, the pharmaceutically acceptable salts of the peptide of the invention are within the scope of this invention. The term "pharmaceutically acceptable salts", as used herein, includes the salts usually used to form metal salts or acid addition salts. The nature of the salt is not critical provided that it is pharmaceutically acceptable. The pharmaceutically acceptable salts of the peptide of the invention can be obtained from organic or inorganic acids or bases. Said salts can be obtained by conventional methods well known by persons skilled in the art.

In a particular and preferred embodiment, the peptide of the invention is a peptide with capacity to bind to scurfin and inhibit its biological activity the amino acid sequence of which comprises or is formed by SEQ ID NO: 1, a variant or fragment thereof, and its pharmaceutically acceptable salts. As shown in the examples attached to this description, said peptide is capable of binding to scurfin and inhibiting its biological activity and, indirectly, of transiently regulating or blocking the immunosuppressive activity of the Treg lymphocytes.

Fusion Protein of the Invention

The peptide of the invention can be fused to another peptide, thus forming a fusion protein. Since the interaction between the peptide of the invention and scurfin must occur inside the cell (e.g., in the cytoplasm and/or in the nucleus), the peptide to which the peptide of the invention is fused is, advantageously, a peptide capable of facilitating the entrance of the peptide of the invention inside the cell.

Therefore, in another aspect, the invention relates to a fusion protein of the invention comprising:
(i) a peptide of the invention, and
(ii) a carrier peptide with capacity to internalize a peptide in a cell.

The characteristics of the peptide of the invention have already been mentioned previously.

A "carrier peptide with capacity to internalize a peptide in a cell", occasionally identified in this description as "carrier peptide", is a peptide capable of traversing the cell membrane and penetrating a cell from the outside, a characteristics which can be conferred to the peptide (e.g., peptide of the invention) to which it is fused (fusion protein of the invention), thus providing an alternative to the transport of peptides of interest (e.g., peptides of the invention) into the target cells. This mechanism of entrance of peptides into the cell is known as "protein transduction or delivery"). Various carrier peptides with capacity to internalize a peptide in a cell are known (Schwarze S. R. et al., Science, 1999 Sep. 3; 285(5433):1569-72; Niesner U. et al., Bioconjug. Chem. 2002 July-August; 13(4):729-36; Ford K. G. et al., Gene Therapy, 2001; 8:1-4; and Gusarova G. A. et al., J. Clin. Invest. 2007 January; 117(1):99-111).

Virtually any carrier peptide with capacity to internalize a peptide in a cell can be used for putting the present invention into practice; nevertheless, in a particular embodiment, said carrier peptide is a peptide comprising a "PTD" ("protein transduction domain") segment. Illustrative non-limiting examples of proteins comprising protein transduction domains (PTDs) include the human immunodeficiency virus 1 (HIV-1) TAT ("transacting translational protein") protein, the *Drosophila antennapedia* homeotic transcription factor (Antp) and the herpesvirus simplex 1 (HSV-1) VP22 DNA-binding protein, although it has also been suggested that other proteins have this property of internalizing peptides in cells, such as influenza virus hemagglutinin, lactoferrin, fibroblast growth factor-1, fibroblast growth factor-2 and the Hoxa-5, Hoxb-4 and Hoxc-8 proteins (Ford K. G. et al., Gene Therapy, 2001; 8:1-4).

In a particular embodiment, said carrier peptide is a peptide derived from the HIV-1 TAT protein, comprising the sequence responsible for peptide transduction, the basic domain (PTD) of which comprises moieties 49-57 of said HIV-1 TAT protein, specifically the amino acid sequence RKKRRQRRR (SEQ ID NO: 9), or moieties 47-57 of said HIV-1 TAT protein, such as the peptide the amino acid sequence of which is YGRKKRRQRRR (SEQ ID NO: 10) or the peptide the amino acid sequence of which is CGISYGRKKRRQRRR (SEQ ID NO: 11).

In another particular embodiment, said carrier peptide is a peptide derived from the *D. antennapedia* Antp protein, comprising the antennapedia homeodomain (AntpHD) comprising the domain responsible for peptide transduction (PTD) [moieties 43-58 of said Antp protein), comprising the amino acid sequence RQIKIWFQNRRMKWKK (SEQ ID NO: 12), or a functional fragment thereof.

In another particular embodiment, said carrier peptide is a peptide derived from the HSV-1 VP22 protein comprising a domain responsible for peptide transduction (PTD).

In another particular embodiment, said carrier peptide is a peptide derived from the ARF ("alternative reading frame") tumor suppressing protein comprising the amino acid sequence responsible for the capacity of the peptide of penetrating the cells, such as the fragment comprising moieties 26-44 of said ARF protein, specifically, the amino acid sequence KFVRSRRPRTASCALAFVN (SEQ ID NO: 13), or a fragment thereof comprising moieties 37-44 of said ARF protein, specifically the amino acid sequence SCALAFVN (SEQ ID NO: 14).

The peptide of the invention can be bound to any of the (amino or carboxyl) terminal ends of the carrier peptide with capacity to internalize a peptide of the invention in a cell. Therefore, in a particular embodiment, the carboxyl-terminal end of the peptide of the invention is bound to the amino-terminal end of said carrier peptide, whereas in another particular embodiment, the amino-terminal end of the peptide of the invention is bound to the carboxyl-terminal end of said carrier peptide.

The peptide of the invention may or may not be directly bound to said carrier peptide with capacity to internalize a peptide in a cell. Therefore, in a particular embodiment, the peptide of the invention [peptide (i)] is directly bound to said carrier peptide [peptide (ii)], whereas in another particular embodiment, the peptide of the invention [peptide (i)] is bound to said carrier peptide [peptide (ii)] through a linker or spacer peptide between said peptides (i) and (ii). As a result, if desired, the fusion protein of the invention can further contain a spacer peptide located between said peptide of the invention [peptide (i)] and said carrier peptide [peptide (ii)]. Said spacer peptide is advantageously a peptide with structural flexibility, such as a peptide giving rise to a non-structured domain. Virtually any peptide with structural flexibility can be used as a spacer peptide; nevertheless, illustrative non-limiting examples of said spacer peptides include peptides containing repeats of amino acid moieties, e.g., of Gly and/or Ser, or any other suitable repeat of amino acid moieties.

If desired, the fusion protein of the invention can optionally include an amino acid sequence useful for the isolation or purification of the fusion protein of the invention. Said sequence will be located in a region of the fusion protein of the invention which does not adversely affect the functionality of the peptide of the invention. Virtually any amino acid sequence which can be used to isolate or purify a fusion protein (generically called tag peptides) can be present in said fusion protein of the invention. By way of a non-limiting illustration, said amino acid sequence useful for isolating or purifying a fusion protein can be, for example, an arginine tag (Arg-tag), a histidine tag (His-tag), FLAG-tag, Strep-tag, an epitope which can be recognized by an antibody, such as c-myc-tag, SBP-tag, S-tag, calmodulin-binding peptide, cellulose-binding domain, chitin-binding domain, glutathione S-transferase-tag, maltose-binding protein, NusA, TrxA, DsbA, Avi-tag, etc. (Terpe K., Appl. Microbiol. Biotechnol. (2003), 60:523-525), β-galactosidase, VSV-glycoprotein (YTDIEMNRLGK) (SEQ ID NO: 15), or an amino acid sequence such as: Ala His Gly His Arg Pro (SEQ ID NO: 16) (2, 4, and 8 copies), Pro Ile His Asp His Asp His Pro His Leu Val Ile His Ser (SEQ ID NO: 17), etc.

Applications of the Peptides and Fusion Proteins of the Invention

The peptide of the invention has capacity to bind to scurfin, and furthermore, advantageously, capacity to inhibit the biological activity of scurfin, therefore it is indirectly capable of transiently regulating or blocking the immunosuppressive activity of Treg lymphocytes. Therefore, an important advantage of the peptide of the invention lies in the fact that by means of its use the immunosuppressive activity of Treg lymphocytes can be transiently or temporarily regulated or blocked. In contrast to other known methods for inhibiting the activity of Treg lymphocytes based on using antibodies against surface markers, the use of the peptides of the invention, i.e., peptides with capacity to bind to scurfin and, particularly, with capacity to inhibit the biological activity of scurfin by means of their direct binding to said protein, does not eliminate Treg lymphocytes, which allows a finer temporary control over their activity. Although there is no intention to be bound by any theory, it is believed that the peptides of the invention, due to their small size, can be introduced in the cells to block the action of scurfin.

Due to the role of Treg lymphocytes in a number of biological processes and to the fact that scurfin is essential for their immunosuppressive activity, the use of the peptides of the invention opens up a window for a potential development of a new family of drugs that are potentially useful in the treatment of neoplastic diseases and of infectious diseases. The inhibition of the biological activity of scurfin allows the peptides of the invention to transiently or temporarily regulate or block the immunosuppressive activity of Treg lymphocytes, therefore therapies can be developed for the treatment of neoplastic diseases or of infectious diseases in which the action of said Treg lymphocytes is furthermore selectively and transiently controlled such that the risk of induction of autoimmunity as a result of their elimination is reduced.

Therefore, the peptides of the invention, as well as the fusion proteins of the invention, can be used in the treatment of a pathology in which it is suitable or necessary to transiently or temporarily regulate or block the immunosuppressive activity of Treg lymphocytes, as occurs in the case of neoplastic diseases or of infectious diseases in which the Treg lymphocytes can have an immunosuppressive role, preventing the correct activation of an effective immune response. It is known, in humans, that Treg lymphocytes are capable of suppressing the beneficial action of antitumor T cells in cases of melanoma (Wang, H. Y., J Immunol, 2005. 174:2661-2670; Viguier, M., F. J Immunol, 2004. 173:1444-1453), lung cancer (Woo, E. Y., Cancer Res, 2001 61:4766-4772), ovarian cancer (Woo, E. Y., Cancer Res, 2001. 61:4766-4772, Curiel, T. J., Nat Med, 2004. 10:942-949), pancreatic cancer and breast cancer (Liyanage, U. K., J Immunol, 2002. 169:2756-2761) as well as in hepatocarcinomas (Ormandy, L. A. Cancer Res, 2005. 65:2457-2464; Kobayashi, N., Clin Cancer Res, 2007. 13:902-911). In infectious diseases, the control exerted by Treg cells can limit the magnitude of effector T responses and cause the failure in the control of the infection. It has thus been described that some viruses, e.g., hepatitis B virus (Xu, D. J Immunol, 2006. 177:739-747), hepatitis C virus (Boettler, T., J Virol, 2005. 79:7860-7867; Cabrera, R. Hepatology, 2004. 40:1062-1071; Rushbrook, J Virol, 2005. 79:7852-7859; Sugimoto, K. Hepatology, 2003. 38:1437-1448) and human immunodeficiency virus (HIV) (Aandahl, E. M. J Virol, 2004. 78:2454-2459; Kinter, A. L. J Exp Med, 2004. 200:331-343; Oswald-Richter, K. PLoS Biol 2004. 2:E198; Weiss, L. Blood, 2004. 104:3249-3256) can use Treg cells to block the antiviral immune response and thus allow the establishment of the persistent chronic infection.

Illustrative examples of the pathologies which can be potentially treated with the peptides and fusion proteins of the invention include neoplastic diseases and infectious diseases. As used herein, the term "neoplastic diseases" includes both tumors (i.e., tissue disorders which cause a increase in volume, particularly, lumps due to an increase in the number of cells forming it, independently of whether they are benign or malignant), and cancer (a disease which is characterized by an uncontrolled proliferation of abnormal cells capable of invading adjacent tissues and disseminating to distant organs). Likewise, the term "infectious diseases" generally relates to diseases caused by infectious agents e.g., viruses, bacteria, fungi, parasites, etc. In this type of infectious or neoplastic (cancerous) process, Treg lymphocytes exert a negative effect, since they are capable of inhibiting the activation of immune responses against infectious or neoplastic processes which would favor the cure.

Illustrative non-limiting examples of viral infections which can be treated with the peptides and fusion proteins of the invention include virtually any infection of viral origin, for example, infections caused by hepatitis B virus, hepatitis C virus, HIV, human papillomavirus, herpes viruses, for example, human herpesviruses such as herpes simplex virus type 1 (HSV-1), herpes simplex virus type 2 (HSV-2), varicella zoster virus (VZV), cytomegalovirus (CMV), human herpesvirus 6 (HHV-6), human herpesvirus 7 (HHV-7), Epstein-Barr virus (EBV), Kaposi's herpesvirus (HHV-8), etc.

Illustrative non-limiting examples of bacterial infections which can be treated with the peptides and fusion proteins of the invention include, although they are not limited to, infections caused by *Mycobacterium leprae*, infections caused by *Mycobacterium tuberculosis*, infections caused by *Yersinia pestis*, gastric infection caused by *Helicobacter pylori*, etc.

Illustrative non-limiting examples of fungal infections which can be treated with the peptides and fusion proteins of the invention include, although they are not limited to, infections caused by *Candida albicans*, infections caused by *Trichophyton rubrum*, infections caused by *Aspergillus* sp., etc.

Illustrative non-limiting examples of parasitic infections which can be treated with the peptides and fusion proteins of the invention include, although they are not limited to, leishmaniasis, e.g., visceral leishmaniasis, infections such as malaria caused by *Plasmodium* parasites, toxoplasmosis, etc.

Illustrative non-limiting examples of neoplastic diseases which can be treated with the peptides and fusion proteins of the invention include, although they are not limited to, papillomas, adenomas, lipomas, osteomas, myomas, angiomas, nevi, mature teratomas, carcinomas, sarcomas or immature teratomas, for example, melanoma, myeloma, leukemia, Hodgkin's lymphoma, basalioma, spinalioma, breast cancer, ovarian cancer, uterine cancer, lung cancer, bronchial cancer, prostate cancer, colon cancer, pancreatic cancer, kidney cancer, esophageal cancer, hepatocarcinoma, head and neck cancer, etc.

Generally, any infectious or neoplastic process in which Treg lymphocytes play an immunosuppressive role, which could affect the cure of the pathology suffered by a subject, can be treated with the peptide of the invention.

Likewise, the peptides and fusion proteins of the invention can be used to enhance antiviral or antitumor vaccines, since their administration after the vaccination, and the subsequent blocking of Treg lymphocytes by the peptides of the invention during their administration, would allow enhancing the response to the components of the vaccine.

It additionally seems that Treg lymphocytes can play a central role in the oral tolerance to an antigen (Huibregtse, I. L. Gastroenterology, 2007. 133:517-528), therefore the peptides of the invention could be used in situations in which this tolerance to orally administered antigens is to be broken.

Pharmaceutical Composition

For its administration to a subject, the peptide of the invention or the fusion protein of the invention will be formulated in a suitable pharmaceutical composition. The term "subject", as used herein, relates to any member of a mammal species and includes but is not limited to domestic animals, primates and humans; the subject is preferably a male or female human being of any age or race.

Therefore, in another aspect, the invention relates to a pharmaceutical composition, hereinafter pharmaceutical composition of the invention, comprising a therapeutically effective amount of a peptide of the invention, or of a fusion protein of the invention, together with at least one pharmaceutically acceptable excipient. Said pharmaceutical composition is useful for its administration and/or application in the human or animal body, preferably in the human body.

The pharmaceutical composition of the invention can contain one or more peptides or fusion proteins of the invention, together with, optionally, one or more alternative compounds regulating or inhibiting the immunosuppressive activity of Treg lymphocytes, different from the peptides and fusion proteins of the invention. Virtually any compound inhibiting or regulating the immunosuppressive activity of Treg lymphocytes, independently of its mechanism of action (e.g., through the inhibition of scurfin or through other mechanisms), different from the peptides and fusion proteins of the invention, can be present, if desired, in the pharmaceutical composition of the invention. Illustrative non-limiting examples of alternative compounds inhibiting or regulating the activity of Treg lymphocytes, different from the peptides and fusion proteins of the invention, which can be used together with the peptides and fusion proteins of the invention include, although they are not limited to, anti-CD25, anti-CTLA4, anti-GITR antibodies, compounds inhibiting cytokines TGF-beta, IL-10 or IL-9, chemotherapeutic compounds such as cyclophosphamide fludarabine, or inhibitors of chemokines CCL17 or CCL22, among others.

The use of the peptides of the invention instead of antibodies has a number of advantages, since said peptides are small molecules, they have a higher diffusion capacity and a shorter half-life. The peptides of the invention have a high affinity for scurfin but are more quickly degraded than antibodies, the possible adverse side effects being able to be controlled by means of a suitable dosage of the peptides of the invention. In addition, most antibodies against Treg lymphocytes cause the elimination of said cells and, therefore, their effect is more long-lasting whereby the risk of inducing autoimmune diseases increases (Stephens, L. A., Proc Natl Acad Sci USA, 2005. 102:17418-17423). The use of fusion proteins of the invention also has a number of advantages since they facilitate the entrance of the peptide of the invention in the cell, whereby the inhibitory activity for the activity of scurfin of the peptides of the invention increases as the interaction between the peptide of the invention and scurfin must be carried out inside the cell (e.g., in the cytoplasm or, perhaps, in the nucleus).

For the treatment of the pathologies for which they are indicated, e.g., infectious or neoplastic diseases, the peptides and fusion proteins of the invention can be administered by any means causing the contact of the peptide of the invention with the site of action thereof in the human or animal body. The amount of peptide, derivative or pharmaceutically acceptable salt thereof, or of fusion protein of the invention, which can be present in the pharmaceutical composition provided by this invention can vary within a wide range.

The dosage for treating said pathologies with the peptides, fusion proteins and/or pharmaceutical compositions of the invention will depend on a number of factors, including the age, condition of the patient, the severity of the disease or pathology, the route and frequency of administration and on the peptide or fusion protein of the invention to be administered.

The pharmaceutical compositions containing the peptide or the fusion protein of the invention can be presented in any dosage form, for example, solid or liquid, and can be administered by any suitable route, for example, oral, parenteral, rectal or topical route, for which they will include the pharmaceutically acceptable excipients necessary for the formulation of the desired dosage form, for example, ointments (lipogels, hydrogels, etc.), eyedrops, aerosol sprays, injectable solutions, osmotic pumps, etc. A review of the different pharmaceutical dosage forms of medicinal products and of the excipients necessary for obtaining them can be found, for example, in "Tratado de Farmacia Galénica", C. Faulí Trillo, 1993, Luzán 5, S. A. Ediciones, Madrid; and in Remington's Pharmaceutical Sciences (A. R. Gennaro, Ed.), $20^{th}$ edition, Williams & Wilkins PA, USA (2000).

The use of the peptides and fusion proteins of the invention in the preparation of the pharmaceutical composition of the invention forms an additional aspect of this invention. Therefore, in another aspect, the invention relates to the use of a peptide of the invention or of a fusion protein of the invention in the preparation of a medicinal product for the treatment of a pathology in which it is suitable or necessary to transiently or temporarily regulate or block the immunosuppressive activity of Treg lymphocytes, such as infectious diseases (e.g., viral infections, bacterial infections, fungal infections, parasitic infections, etc.) and neoplastic diseases, e.g., cancer and tumors.

Likewise, in another aspect, the invention relates to the use of a peptide of the invention or of a fusion protein of the invention in the treatment of a pathology in which it is suitable or necessary to transiently or temporarily regulate or block the immunosuppressive activity of Treg lymphocytes, such as infectious diseases (e.g., viral infections, bacterial infections, fungal infections, parasitic infections, etc.) and neoplastic diseases, e.g., cancer and tumors.

Obtaining the Peptides of the Invention

The peptide of the invention can be obtained by conventional synthetic methods, for example, by means of solid phase synthesis techniques, and purified by means of conventional methods, for example, by means of high performance liquid chromatography (HPLC). Additionally, if desired, it can be analyzed by means of conventional techniques, for example, by means of sequencing and mass spectrometry, amino acid analysis, nuclear magnetic resonance, etc. By way of a non-limiting illustration, the peptide of the invention can be obtained by means of peptide synthesis following conventional procedures (Merrifield R B. J Am Chem Soc 1963; 85:2149-2154) using Atherton's Fmoc variant (Atherton, E., Logan, J. C. and Sheppard, R. C. 1989. Peptide synthesis II. Procedures for solid phase synthesis using N-fluorenyl methoxycarbonyl amino acids on polyamide supports. Synthesis of substance P and of acyl carrier protein 65-74 decapeptide. J. Chem. Soc. Perkin Trans. 1:538). The purity of the peptide obtained can be determined by means of reversed phase HPLC and/or mass spectrometry, for example.

The fusion protein of the invention can be obtained by means of a coupling reaction of the peptide of the invention and of the carrier peptide with capacity to internalize a peptide of the invention in a cell, which may have been obtained by conventional synthetic methods, such as those which have been previously mentioned (e.g., solid phase chemical synthesis), or by means of recombinant techniques.

Alternatively, the peptide of the invention and the fusion protein of the invention can be obtained by means of recombinant DNA technology. Therefore, in another aspect, the invention provides a DNA sequence encoding a peptide or a fusion protein of the invention. Said DNA sequence can be easily deduced from the amino acid sequence of the peptide or of the fusion protein of the invention.

Said DNA sequence can be contained in a DNA construct. Therefore, in another aspect, the invention provides a DNA construct comprising a DNA sequence encoding a peptide or fusion protein of the invention. Said DNA construct can contain, operatively bound, a sequence regulating the expression of the DNA sequence encoding the peptide or fusion protein of the invention. Control sequences are sequences controlling and regulating the transcription and, where appropriate, the translation of the peptide or fusion protein of the invention, and include promoter, terminator sequences etc., functional in transformed host cells comprising said DNA sequence or construct. In a particular embodiment, said expression control sequence is functional in bacteria. Said DNA construct advantageously further comprises a marker or gene encoding a motif or a phenotype which allows selecting the transformed host cell with said DNA construct. The DNA construct provided by this invention can be obtained by means of using techniques that are widely known in the state of the art (Sambrook et al., "Molecular cloning, a Laboratory Manual", $2^{nd}$ ed., Cold Spring Harbor Laboratory Press, N.Y., 1989 Vol 1-3).

The DNA sequence or the DNA construct provided by this invention can be inserted in a suitable vector. Therefore, in another aspect, the invention relates to a vector, such as an expression vector, comprising said DNA sequence or construct. The choice of the vector will depend on the host cell in which it will be subsequently introduced. By way of example, the vector wherein said DNA sequence is introduced can be a plasmid or a vector which, when it is introduced in a host cell, is or is not integrated in the genome of said cell. Said vector can be obtained by conventional methods known by persons skilled in the art (Sambrook et al., 1989, mentioned above).

In another aspect, the invention relates to a host cell, such as a transformed host cell, comprising a DNA sequence or a DNA construct provided by this invention or a vector as has been previously mentioned. Said cell can be a prokaryotic or eukaryotic cell.

Likewise, in another aspect, the invention relates to a process for producing a peptide of the invention or a fusion protein of the invention comprising growing a host cell comprising the sequence, DNA construct or vector provided by this invention under conditions allowing the production of said peptide or fusion protein of the invention and, if desired, recovering said peptide or fusion protein of the invention. The conditions for optimizing the culture of said host cell will depend on the host cell used. If desired, the process for producing the peptide or the fusion protein of the invention further includes the isolation and purification of said peptide or fusion protein.

In addition, said DNA sequences and DNA constructs provided by this invention can be used in the preparation of vectors and cells for treating a pathology in which it is suitable or necessary to transiently regulate or block the immunosuppressive activity of Treg lymphocytes. Therefore, in another aspect, the invention relates to the use of said DNA sequences and DNA constructs in the preparation of vectors and cells for the treatment of a pathology in which it is suitable or necessary to transiently regulate or block the immunosuppressive activity of Treg lymphocytes, for example, viral, bacterial, fungal, parasitic infections, etc., and neoplastic diseases. According to this aspect of the invention, said DNA sequence or construct can be put in contact with a gene transfer vector, such as a viral or non-viral vector. Suitable viral vectors for putting this embodiment of the invention into practice include, but are not limited to, adenoviral vectors, adeno-associated vectors, retroviral vectors, lentiviral vectors, alphaviral vectors, herspesviral vectors, coronavirus-derived vectors, etc. Suitable non-viral type vectors for putting this embodiment of the invention into practice include, but are not limited to naked DNA, liposomes, polyamines, dendrimers, cationic glycopolymers, liposome-polycation complexes, proteins, receptor-mediated gene transfer systems, etc.

Initial Identification of the Peptides of the Invention

The technique associated to phage libraries has been used to initially identify peptides with capacity to bind to scurfin. This technique allows identifying peptides having a high-affinity binding with a certain protein (e.g., scurfin) and subsequently quantifying, by means of in vitro assays, their capacity to inhibit the biological activity of the protein in question. In this case, said protein is scurfin and the inhibition of its biological activity allows indirectly regulating or blocking the immunosuppressive activity of Treg lymphocytes. The sequence of the peptides binding to scurfin, inhibiting its biological activity, can be deduced from the corresponding DNA sequence after several biopanning cycles, generally 3. The use of phage libraries for identifying inhibitors of certain products has been described, for example, by Chirinos-Rojas C. L. et al., in Immunology, 1999, January 96(1):109-113; McConnell S. J., et al., in Gene 1994, Dec. 30, 151(1-2):115-118; or by Smith G. P., Science, 1985, Jun. 14, 228(4705): 1315-1317.

Therefore, in another aspect, the invention relates to a method for identifying peptides with capacity to bind to scurfin comprising:

(i) using a phage library comprising a plurality of filamentous phages, the genome of each of said phages containing a nucleotide sequence encoding a different peptide linked to the gene of a phage coat protein, whereby each phage contains a different peptide genetically fused to a phage coat protein;

(ii) selecting, by means of an affinity assay, the phages containing the peptides binding to scurfin with higher affinity; and (iii) determining the sequence of the peptides binding to scurfin from the corresponding DNA sequences inserted in the phages selected in step (ii) and encoding said peptides binding to scurfin.

In a particular embodiment, for the purpose of obtaining peptides with a length of 15 amino acids capable of binding to scurfin with high affinity with possible inhibitory activity for its biological activity, a phage library was used which was formed by a plurality of filamentous bacteriophages (M13), each of them containing a different peptide, of 15 amino acids, genetically fused to a phage coat protein, in this case bound to the N-terminal end of the pIII coat protein. The phage thus displays on its surface a peptide of 15 amino acids, in each of the 5 molecules of the surface protein, whereas it internally contains the DNA encoding said peptide sequence. In the phage libraries, the sequence encoding the peptide comes from a degenerated sequence in each of the 15 positions with the 20 natural amino acids, which allows the display of $1.1 \times 10^{12}$ possible sequences of 15 amino acids in different phages. The 1 to 1 physical ratio between the peptide sequence and the DNA encoding it in the bacteriophage allows selecting, from a large number of variants, those sequences binding specifically to scurfin. This process is carried out by means of an affinity assay.

In a particular embodiment, said affinity assay consists of an in vitro selection protocol called biopanning. Briefly, said technique consists of incubating a set of phages representing, for practical purposes, all the variants of peptides of 15 amino acids (in this case), in a plate coated with scurfin, correctly displayed for its interaction with the peptides carried by the phages. After an incubation, the unbound phages are eliminated by means of washings and the specifically bound phages are subsequently eluted by means of a pH decrease which breaks the molecular interactions between scurfin and the peptides displayed by the phages. The eluted phages are then amplified by means of infection in a bacterial strain. The process is repeated a total of 3 rounds, such that the content of phages binding specifically and with high affinity to scurfin is enriched. The concentration of scurfin used to block the plates is progressively reduced in each round, for example, from 2.5 to 0.02 μg/mL and, finally, 0.002 μg/mL. The phages selected in each round thus have a higher degree of affinity for scurfin. At the end of the process, the phages which have been selected for their affinity for scurfin are sequenced with primers. This allows obtaining the sequences of the peptides displayed in the phages. After this screening is carried out, assays for confirming the capacity of interaction between said peptides and scurfin can be carried out by means of the biomolecular interaction surface plasmon resonance (SPR) technique, as shown in FIG. 1 and which shows how peptide P60 (SEQ ID NO: 1), identified by means of this technique, specifically binds to scurfin.

The following examples illustrate the invention and must not be considered as limiting the scope thereof.

EXAMPLE 1

Selection of Peptides with Capacity to Bind to Scurfin

The selection of peptides with capacity to bind to scurfin and possible inhibitory activity for its biological activity was carried out by means of an in vitro selection technique based on the technology developed from phage libraries.

1.1 Production of Scurfin

To produce scurfin, plasmid pDEST15-FOXP3, a scurfin expression vector bound to glutathione-S-transferase (GST) was used as a fusion protein, kingly provided by Dr. Ignacio Casal (Centro Nacional de Investigaciones Oncológicas, CNIO, Madrid, España). Said plasmid was cloned into *Escherichia coli* BL21 bacteria competent for the expression and subsequent purification of the protein (scurfin). The expression of said protein was carried out from a culture of 0.5 liters of LB culture medium (Sigma, St Louis). The bacterial pellet was lysed in a French press (Thermo Electron Corporation), such that the scurfin remained in the supernatant. The purification of scurfin was carried out by means of affinity chromatography using GSTrap affinity columns (Ref 17513001, Amersham, Pharmacia) and the platform of an FPLC (fast protein liquid chromatography) chromatograph (Akta FPLC, Amersham Biosciences). A Western Blot was carried out with the pooled fractions to verify the existence of the protein, using anti-Foxp3 antibodies (ab10564, Abcam). Once scurfin was isolated and purified, the binding/elution rounds with the phage library were started.

1.2 Selection of Peptides by Means of the Phage Library and Biopanning Technique The technology associated to phage libraries has been used to identify peptides with capacity to bind to scurfin. This technique allows identifying peptides having a high-affinity binding with a certain protein (in this case, scurfin) and subsequently quantifying, by means of in vitro assays, the capacity of the different peptides to inhibit the biological activity of said protein. The sequence of the peptides binding to scurfin can be deduced from the corresponding DNA sequence after several biopanning cycles (generally 3).

The phage library used to carry out this example contains $2\times10^8$ different clones and has been provided by the laboratory of George P. Smith (Division of Biological Sciences Tucker Hall, University of Missouri, USA). The phages present in said phage library were amplified and purified before carrying out the selection (biopanning). To that end, 10 μl of said phage library were amplified using *E. coli* K91Kan (supplied by George P. Smith, Division of Biological Sciences Tucker Hall, University of Missouri) as a host strain and subsequently purified by means of 2 precipitations with polyethylene glycol (PEG)/NaCl and a CsCl gradient centrifugation. The titer of the phage suspension, calculated by spectrometry was $3.82\times10^{14}$ virions/ml and the number of infectious particles was $1.3\times10^{13}$ TU/ml. Before starting the selection assay, a fraction of said phage suspension was sequenced to verify that the amplification had not affected the diversity of the clones.

The process for selecting peptides with capacity to bind to scurfin, potentially useful as inhibitors of its biological activity, comprises putting scurfin in contact with the peptides displayed by the phage library. To that end, the wells of a 96-well plate were coated with scurfin (adding scurfin in a carbonate buffer to said wells and leaving to incubate for 16 hours at 4° C.), 10 μl of the phage library were added at a concentration of $3\times10^4$ virus/ml and it was left to incubate for 1-2 hours at room temperature (20-22° C.). The unbound phages were then eliminated by means of washings with PBS/Tween (phosphate buffered saline/polyoxyalkylene derivatives of sorbitan fatty acid esters), such that only the specific phages of scurfin remained bound to the plate. These phages bound specifically to scurfin were eluted by means of pH decrease (elution buffer) which breaks the molecular interactions between scurfin and the peptides displayed by the phages. The eluted phages were amplified by means of infection in a bacterial strain (*E. coli* K91Kan), this process being repeated a total of 3 more of binding/elution rounds, each time with less amount of scurfin adhered to the wells (being progressively reduced in each round from 2.5 μg/ml to 0.02 μg/ml, and finally to 0.002 μg/ml), such that in each round the phages with higher scurfin-binding affinity were selected. Thus, in the final round, colonies of bacteria infected by a single phage, having in the degenerated region of its genome a single sequence encoding a single peptide (the selection of the bacterial colonies was carried out in the presence of tetracycline the resistance of which is given by a gene of resistance to said antibiotic present in the genome of the phages, such that, in this way, only the colonies infected by the phages grow and each colony contains the genome of a single phage to which the sequence of a single peptide displayed on its surface corresponds). The sequencing of this region allows knowing its DNA sequence and therefore the sequence of the peptide capable of binding to scurfin, potentially an inhibitor of the activity of scurfin.

From colonies of bacteria infected by phages, derived from the last biopanning selection round, the DNA thereof was extracted and the portion of the genome including the region corresponding to the peptides displayed in the pIII protein of the phage was sequenced using the specific primer (SEQ ID NO:5) which hybridizes close to that region. Thus, 47 peptides were obtained.

To restrict the number of peptides to be assayed, a commercial ELISA was carried out, based on a anti-M13 monoclonal antibody of the phage (HRP/Anti-M13 monoclonal Conjugate (Ref 27942101, Amersham Pharmacia Biotech)), for the purpose of only selecting the phages with higher affinity for scurfin. Briefly, the ELISA was carried out using Maxisorp plates (Nunc, Ref: 442404) coated with scurfin. The selected phages were dispensed in the wells of the ELISA plate and, after successive washings, the plate was developed with the anti-M13 monoclonal antibody. The wells with optical densities greater than their respective negative controls (wells without scurfin) contained the most specific peptides for scurfin. Thus, 25 of the 47 initial phages were selected. The 25 peptides selected were chemically synthesized using the Fmoc technology in the laboratory of the inventors for their use in subsequent assays. After carrying out several in vitro assays to measure the capacity of those peptides to inhibit the immunosuppressive action of Treg cells, the peptide identified as P60 (SEQ ID NO: 1) was selected because it had the highest inhibitory activity in such assays (Example 2).

1.3 Determination of the Capacity of Peptide P60 (SEQ ID NO: 1) to Bind to Scurfin by Means of Surface Plasmon Resonance (SPR)

The capacity of peptide P60 (SEQ ID NO: 1) to bind to scurfin was verified by means of the biomolecular interaction surface plasmon resonance (SPR) using the Biosensor BIAcore X (BIAcore, AB, Uppsala, Sweden). Scurfin, produced in E. coli and purified by affinity using GSTrap columns (Amersham, Pharmacia), was covalently immobilized on the surface of the flow cell 2 (FC2) of a CM5 chip (Sensor Chip CM Ref 116Br-1000-14, BIAcore, General Electrics), as described in De Crescenzo et al. (JBC 2001, Vol 276; 29632-29643). Flow cell 1 (FC1), on the surface of which scurfin is not immobilized, was used as a reference reflow cell. The solutions of each peptide (10 µM) were injected three times in a 10 mM Hepes buffer, 150 mM NaCl, pH 7.4 at a flow of 30 µl/min. The binding curves were processed by means of subtracting the response in FC1 from that obtained in FC2. The response in equilibrium was compared between peptide P60 (SEQ ID NO: 1) and an irrelevant control peptide of the same size (length), specifically, the peptide the amino acid sequence of which is shown in SEQ ID NO: 6, corresponding to amino acids 123-137 of the human CD81 receptor. Each response was multiplied by a mass correction factor: MW(P60)/MW(P), wherein MW(P60) is the molecular weight of peptide P60 (SEQ ID NO: 1) and MW(P) is that of the control peptide. As can be seen in FIG. 1, peptide P60 (SEQ ID NO: 1) gives a positive signal proving its capacity to bind specifically to the scurfin protein.

1.4 Generation of Truncated Forms of Peptide P60 (SEQ ID NO: 1), by Deletion of Amino Acids from the Amino- or Carboxyl-Terminal Ends, and Evaluation of their Capacity to Bind to Scurfin For the purpose of evaluating the importance of the amino acids placed at the amino-terminal and carboxyl-terminal ends of peptide P60 (SEQ ID NO: 1), truncated forms of said peptide P60 (SEQ ID NO: 1) were chemically synthesized as has been mentioned above, and the capacity of said truncated forms to bind to scurfin was assayed by means of SPR, according to the protocol previously described in section 1.3.

The chemically synthesized truncated forms were the peptides or truncated forms of P60 identified as:
T(1-13) (SEQ ID NO: 2) [amino acids 1-13 of P60],
T(1-14) (SEQ ID NO: 3) [amino acids 1-14 of P60], and
T(2-15) (SEQ ID NO: 4) [amino acids 2-15 of P60].

Likewise, the capacity of said peptides (SEQ ID NO: 2, SEQ ID NO: 3 and SEQ ID NO: 4) to bind to scurfin was assayed by means of SPR in the previously mentioned conditions. The results obtained show that the elimination of an amino acid in an amino-terminal position inhibits the capacity of the peptide to bind to scurfin. However, the elimination of residues 14 or 15 from the carboxyl-terminal end does not destroy the capacity of the peptide to bind to scurfin (FIG. 2).

EXAMPLE 2

Effect of Peptide P60 (SEQ ID NO: 1) on the Immunosuppressive Activity of the Karpas 299 Human Cell Line After verifying and confirming its profile, in vitro assays were carried out using the Karpas 299 human cell line (ACC-31, DSMZ, Germany), derived from a human lymphoma with a regulatory T cell [Treg lymphocytes] profile (Wolke et al Int J Mol. Med. 2006 February; 17(2):275-8), the need to isolate CD4+CD25+ cells is thus prevented.

To evaluate the effect of peptide P60 (SEQ ID NO: 1) on the immunosuppressive activity of the Karpas 299 cell line, a "mixed lymphocyte reaction" (MLR) assay was carried out using peripheral blood mononuclear cells (PBMCs) from 2 donors in the presence or absence of the Karpas 299 cell line. This assay (MLR) is based on co-culturing lymphocytes of a different origin, with different histocompatibilities, which will recognize one another as foreign. This reaction makes lymphocytes proliferate, secreting cytokines. For this assay, 100,000 cells of each donor (positive MLR control) were cultured in a 96-well plate, alone or in the presence of 10,000 cells of the Karpas 299 cell line.

Figure 3:
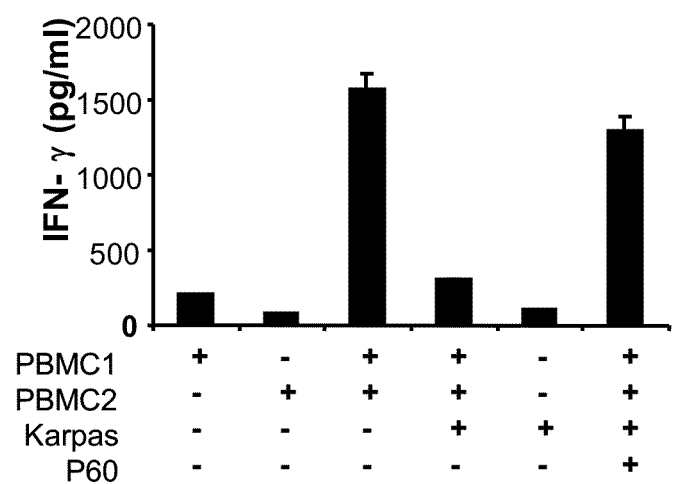
FIG. 3 is a bar graph showing the suppressive activity of the Karpas 299 human cell line (ACC-31, DSMZ, Germany). With these cells, a mixed lymphocyte reaction (MLR) was conducted in which the IFN-γ levels produced after culturing peripheral blood mononuclear cells (PBMCs) from 2 donors in the presence or absence of the Karpas 299 cell line were measured. When the PBMCs of 2 different donors are cultured, an immune response known as mixed lymphocyte response occurs, which involves an activation of cell proliferation and the production of cytokines such as IFN-γ by allogeneic recognition through the reaction between the major histocompatibility complex (MHC) and the T cell receptor (TCR). This response is inhibited if Karpas 299 cells (with the phenotype and activity of Treg lymphocytes) are added. Legends: PBMC1 ($1 \times 10^5$ cells/well), peripheral blood lymphocytes from a healthy donor (1); PBMC2 ($1 \times 10^5$ cells/well), peripheral blood lymphocytes from another healthy donor (2) different from donor (1); Karpas, Karpas 299 cell line ($1 \times 10^4$ cells/well). The same figures show how peptide P60 (SEQ ID NO: 1) (100 μM) is capable of restoring the production of IFN-γ by T lymphocytes (measured in the culture supernatants by an ELISA assay, BD Biosciences), inhibiting the suppressive action of Karpas 299 cells.

After 48 hours, the supernatants were extracted to measure interferon-gamma (IFN-γ) by means of a commercial ELISA (Ref 555138, Pharmingen, San Diego, Calif., United States). In this case, it is not possible to measure the cell proliferation because the presence of the Karpas 299 cell line masks any possible effect in the proliferation of the MLR. The results of the measurement of IFN-γ are shown in FIG. 3 and provide information about the suppressive activity of the Karpas 299 cell line. In this assay of inhibition of the MLR due to the presence of the Karpas 299 cell line, the capacity of peptide P60 (SEQ ID NO: 1) to restore the production of IFN-γ due to the MLR was analyzed. FIG. 3 shows that the addition of peptide P60 (SEQ ID NO: 1) (100 µM) to the co-culture of the MLR with the Karpas 299 cell line is capable of partly recovering the production of IFN-γ which is observed in the absence of the Karpas 299 cells.

EXAMPLE 3

Effect of Peptide P60 (SEQ ID NO: 1) on the Immunosuppressive Activity of Human and Mouse Treg Lymphocytes 3.1 Effect of Peptide P60 (SEQ ID NO: 1) on the Immunosuppressive Activity of Human Treg Lymphocytes The inhibitory capacity of peptide P60 (SEQ ID NO: 1) on the immunosuppressive activity of human Treg lymphocytes was analyzed by means of 2 different assays:
a) by means of an assay based on a mixed lymphocyte reaction (MLR); and
b) by means of an assay based on the measurement of the production of IFN-γ in a culture of human CD4 effector T lymphocytes cultured with microspheres containing anti-CD3 and anti-CD28 antibodies adhered to their surface, in the presence or absence of Treg lymphocytes.

3.1.1 Assay Based on the Mixed Lymphocyte Reaction (MLR)

Figure 4:
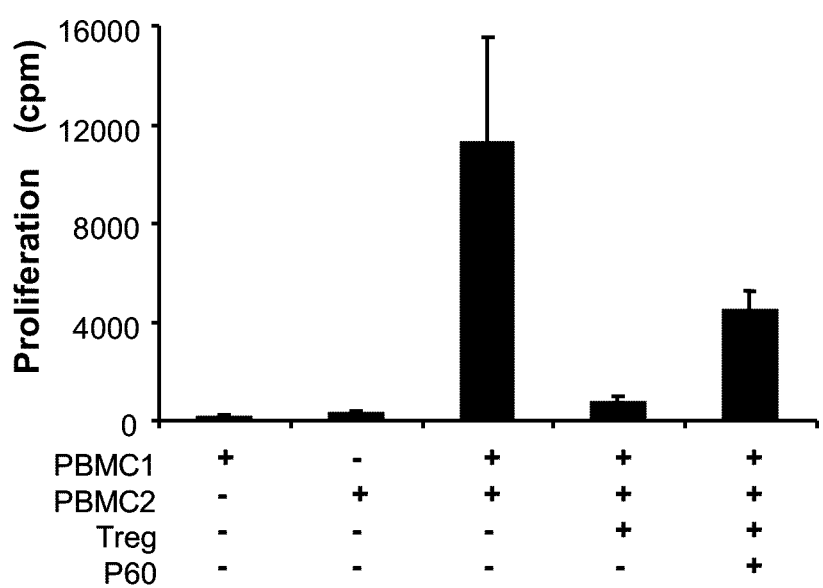
FIG. 4 is a bar graph showing the effect of peptide P60 (SEQ ID NO: 1) on the action of human Treg lymphocytes (purified from peripheral blood from a healthy donor using a Miltenyi Biotech kit, Ref 130-091-301) on a mixed lymphocyte reaction (MLR). PBMCs derived from two blood donors ($1 \times 10^5$ cells/well of each donor) were mixed and incubated in the presence or absence of Treg lymphocytes ($2 \times 10^4$ cells/well) (obtained from one of them) and peptide P60 (SEQ ID NO: 1) (100 µM). After 3 days of culture, the cell proliferation was measured by means of a conventional tritiated thymidine incorporation assay. As can be seen, Treg lymphocytes are capable of inhibiting the MLR and peptide P60 (SEQ ID NO: 1) is capable of reducing the immunosuppressive effect of human Treg lymphocytes on the MLR.

To carry out the assay based on a mixed lymphocyte reaction (MLR), such as that shown in Example 2, peripheral blood mononuclear cells (PBMCs) from 2 donors were mixed together with CD4+CD25+ Treg cells (Treg lymphocytes) purified from one of them, by means of using a commercial kit (Ref 130091072, Miltenyi Biotec, Bergisch Gladbach, Germany) following the instructions of the manufacturer. After the purification, the cells were analyzed by flow cytometry, a purity of approximately 90% being obtained in all the assays. This MLR assay was carried out incubating $10^5$ PBMC cells from each donor and $2 \times 10^4$ Treg lymphocytes in the presence or absence of peptide P60 (SEQ ID NO: 1), for the purpose of assaying its capacity to block the inhibitory effect of human Treg lymphocytes. After 3 days of culture, 0.5 µCi/well of tritiated thymidine (Amersham, Pharmacia) and after 16 hours, the plates were harvested using a harvester (Filtermate 96 harvester; Packard Instrument, Meriden, Conn.) and the radioactivity incorporated to the cell DNA was counted (as a measurement of the cell proliferation) by means of a scintillation counter (Topcount; Packard Instrument). The results of this assay are shown in FIG. 4, in which it can be seen that the mixture of the PBMCs of 2 donors promotes cell proliferation, measured as the incorporation of radioactive thymidine, and that the addition of Treg lymphocytes is capable of inhibiting said cell proliferation; and it is furthermore observed that the addition of peptide P60 (SEQ ID NO: 1) to those co-cultures is capable of partly restoring the MLR, blocking the immunosuppressive effect of human Treg lymphocytes.

3.1.2 Assay Based on the Measurement of IFN-γ

Figure 5:
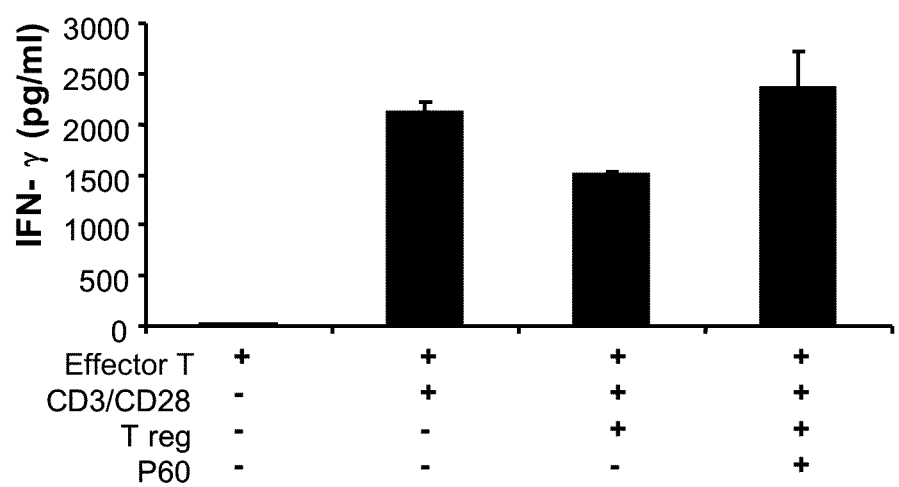
FIG. 5 is a bar graph showing the effect of peptide P60 (SEQ ID NO: 1) on the action of natural human Treg lymphocytes (purified from peripehral blood from a healthy donor) on the response of effector cells against the stimulation with bead-bound anti-CD3/CD28 antibodies (Dynabeads® CD3/CD28, Ref 111-31, Dynal). The effector T lymphocytes obtained from a healthy donor ($1 \times 10^5$ cells/well) were cultured in the presence or absence of anti-CD3/CD28 stimulus, Treg lymphocytes ($2 \times 10^4$ cells/well) and peptide P60 (SEQ ID NO: 1) (100 µM). After 48 hours of culture, the presence of IFN-γ in the culture supernatants was measured by means of a commercial ELISA. As can be seen, peptide P60 (SEQ ID NO: 1) is capable of inhibiting the immunosuppressive effect of human Treg lymphocytes on the activation with anti-CD3/CD28.

This assay is based on the measurement of the production of IFN-γ in a culture of $10^5$ human CD4 effector T lymphocytes cultured with microspheres containing anti-CD3 and anti-CD28 antibodies adhered to their surface (Dynabeads® CD3/CD28; Ref 111.31, Dynal), in the presence or absence of $2 \times 10^4$ human Treg lymphocytes (purified as indicated above). This assay was carried out in the presence or absence of peptide P60 (SEQ ID NO: 1) to assess its inhibitory effect of Treg lymphocytes. After 48 hours of culture, the presence of IFN-γ in the culture supernatants was measured by means of a commercial ELISA (Ref 555138, Pharmingen). FIG. 5 shows that the microspheres containing anti-CD3 and anti-CD28 antibodies stimulate the production of IFN-γ by T lymphocytes and that the addition of Treg cells to the culture is capable of inhibiting said production of IFN-γ. The addition of peptide P60 (SEQ ID NO: 1) to these co-cultures is again capable of blocking the inhibitory effect of human Treg lymphocytes, partly restoring the production of IFN-γ in response to the stimulus.

3.2 Effect of Peptide P60 (SEQ ID NO: 1) on the Immunosuppressive Activity of Murine Treg Lymphocytes The inhibitory capacity of peptide P60 (SEQ ID NO: 1) on the immunosuppressive activity of murine Treg lymphocytes was analyzed by means of 3 different assays:
a) by means of an assay based on the activation of splenocytes;
b) by means of a mixed lymphocyte reaction (MLR) assay; and
c) by means of an assay based on co-culturing transgenic mouse splenocytes with Treg lymphocytes.

3.2.1 Assay Based on the Activation of Splenocytes

Figure 6:
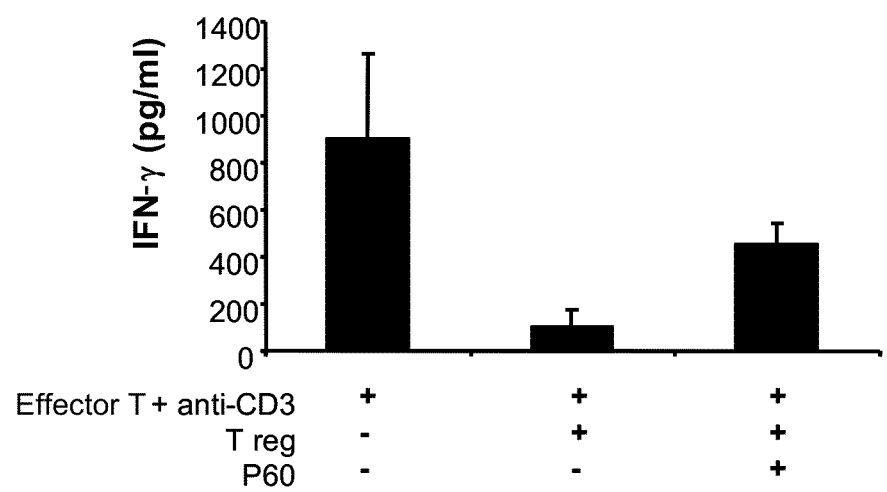
FIG. 6 is a bar graph showing the effect of peptide P60 (SEQ ID NO: 1) on the action of natural murine Treg lymphocytes (purified from mouse splenocytes by means of using a Miltenyi Biotech kit, Ref: 130-091-041) on the production of IFN-γ by effector T cells against the stimulation with anti-CD3 antibodies (BD-Biosciences). The BALB/c mouse splenocytes were cultured ($1 \times 10^5$ cells/well) in the presence or absence of anti-CD3 antibodies (0.5 µg/ml), Treg lymphocytes ($2 \times 10^4$ cells/well) and peptide P60 (SEQ ID NO: 1) (100 µM). As can be seen, peptide P60 (SEQ ID NO: 1) is capable of inhibiting the immunosuppressive effect of Treg lymphocytes on the production of IFN-γ (measured by means of a commercial ELISA) by the effector cells in response to the stimulus with anti-CD3.

Firstly, assays of activation of BALB/c mouse splenocytes (Charles River) in the presence of anti-CD3 antibodies (Ref 553057, BD Biosciences) were carried out. To that end, $10^5$ BALB/c mouse splenocytes were cultured in the presence or absence of anti-CD3 antibodies, $2 \times 10^4$ murine Treg lymphocytes and peptide P60 (SEQ ID NO: 1), it being observed that peptide P60 (SEQ ID NO: 1) (100 µM) is capable of inhibiting the immunosuppressive effect of Treg lymphocytes on the production of IFN-γ by the effector cells in response to the stimulus with anti-CD3 (FIG. 6).

3.2.2 Mixed Lymphocyte Reaction Assay (MLR)

Figure 7:
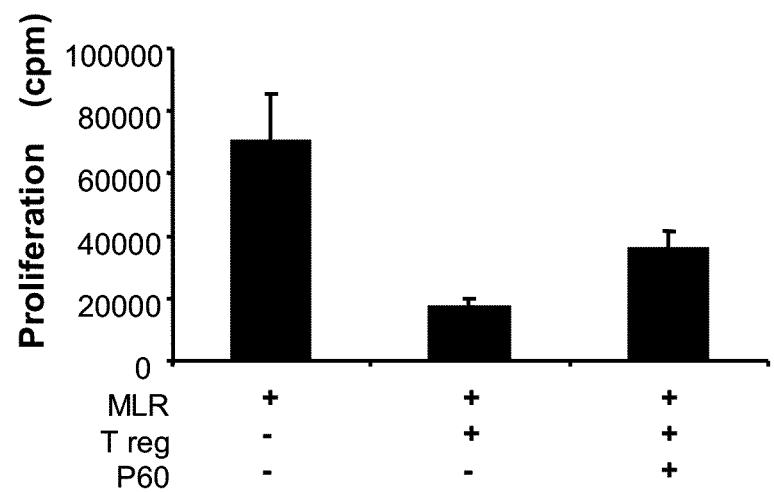
FIG. 7 is a bar graph showing the effect of peptide P60 (SEQ ID NO: 1) on the action of natural murine Treg lymphocytes (purified from mouse splenocytes) on the response of effector cells against the stimulation by a mixed lymphocyte reaction (MLR) (measurement of the cell proliferation by means of a conventional tritiated thymidine incorporation assay). The effector lymphocytes isolated from BALB/c mice ($1 \times 10^5$ cells/well) were co-cultured with purified dendritic cells from C57BL/6 mice, in the presence or absence of BALB/c Treg lymphocytes ($2 \times 10^4$ cells/well) and in the presence or absence of peptide P60 (SEQ ID NO: 1) (100 µM). As can be seen, peptide P60 (SEQ ID NO: 1) is capable of inhibiting the immunosuppressive effect of Treg lymphocytes on the proliferation of effector cells.

Secondly, mixed lymphocyte reaction (MLR) assays were carried out. The effector lymphocytes isolated from BALB/c mice ($10^5$ cells/well) were co-cultured with purified dendritic cells from C57BL/6 mice (Charles River), in the presence or absence of BALB/c Treg lymphocytes and in the presence or absence of peptide P60 (SEQ ID NO: 1) (100 µM). The measurement of the cell proliferation was carreid out by means of a conventional tritiated thymidine incorporation assay as has been previously described. The results obtained show that peptide P60 (SEQ ID NO: 1) is capable of inhibiting the immunosuppressive effect of Treg lymphocytes on the proliferation of effector cells in response to an MLR (FIG. 7).

Figure 8:
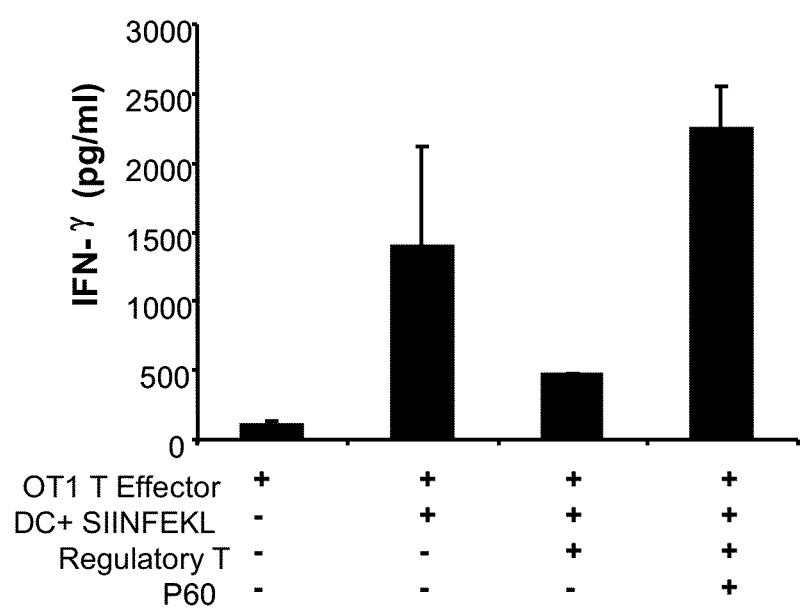
FIG. 8 is a bar graph showing the effect of peptide P60 (SEQ ID NO: 1) on the action of natural murine Treg lymphocytes (purified from mouse splenocytes) on the response of effector cells against the stimulation by an antigen (measured as production of IFN-γ to the culture supernatant). The effector lymphocytes isolated from OT1 trransgenic mice ($1 \times 10^5$ cells/well) (Example 3 (section 3.2.3)) were co-cultured with dendritic cells DC from C57BL/6 mice and the peptide SIINFEKL (SEQ ID NO: 7) (10 µg/ml), in the presence or absence of BALB/c Treg lymphocytes ($2 \times 10^4$ cells/well) and in the presence or absence of peptide P60 (SEQ ID NO: 1) (100 µM). As can be seen, the peptide P60 (SEQ ID NO: 1) is capable of inhibiting the immunosuppressive effect of the Treg lymphocytes sobre the production of IFN-γ by the specific effector cells of this peptide antigen.

3.2.2 Assay Based on Co-Culturing of Transgenic Mouse Splenocytes with Treg Lymphocytes Thirdly, the effect of peptide P60 (SEQ ID NO: 1) was measured in an assay based on co-culturing splenocytes from OT-1 transgenic mice (the T lymphocytes of which have a specific T cell receptor for the peptide SIINFEKL (SEQ ID NO: 7) of ovalbumin, which were kindly provided by Dr Melero, CIMA Pamplona) with Treg lymphocytes in the presence of antigen (SEQ ID NO: 7) and in the presence or absence of Treg lymphocytes. FIG. 8 shows the effect of peptide P60 (SEQ ID NO: 1) on the action of natural murine regulatory T cells (purified from mouse splenocytes) on the response of effector cells against the stimulation by an antigen (measured as production of IFN-γ to the culture supernatant). The effector lymphocytes isolated from OT-1 transgenic mice ($10^5$ cells/well) were co-cultured with dendritic cells from C57BL/6 mice and the peptide SIINFEKL (SEQ ID NO: 7) (10 µg/ml), in the presence or absence of $2 \times 10^4$ BALB/cregulatory T cells and in the presence or absence of peptide P60 (SEQ ID NO: 1) (100 µM). As can be observed, peptide P60 (SEQ ID NO: 1) is capable of inhibiting the immunosuppressive effect of Treg lymphocytes on the production of IFN-γ (measured by a commercial ELISA (Ref: 555138, Pharmingen, San Diego, Calif.)) by the specific effector cells of this peptide antigen.

EXAMPLE 4

Figure 9:
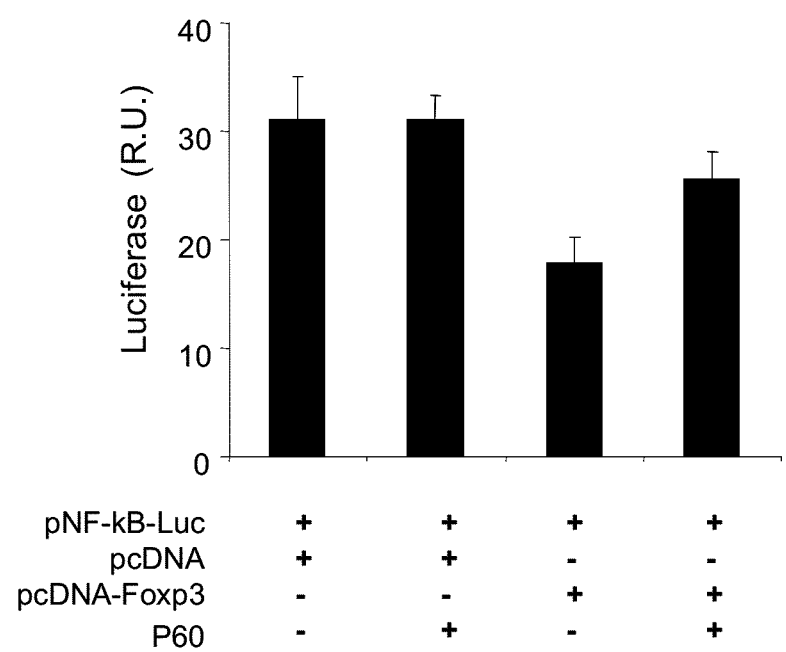
FIG. 9 is a bar graph showing the effect of peptide P60 (SEQ ID NO: 1) on the inhibition of the activation of transcription factor NF-κB by scurfin. The 293 cells were transfected with plasmid pNF-kB-Luc (Clontech, Ref 631904) expressing luciferase under a promoter inducible by transcription factor NF-κB, in the presence or absence of plasmid pcDNA, pcDNA-Foxp3 and peptide P60 (SEQ ID NO: 1) (100 µM). As can be seen, the presence of scurfin in the cells inhibits the expression of luciferase and the presence of peptide P60 (SEQ ID NO: 1) restores this expression. R.U.: relative units.

Effect of the Inhibition of Scurfin on the Activation of Transcription Factor NF-κB It has been described that the presence of scurfin can inhibit the activation of the transcription factor NF-kB in 293 cells (Betelli et al, Proc Natl Acad Sci USA. 2005 102:5138-43). Based on this work, the effect of the addition of peptide P60 (SEQ ID NO: 1) to a culture of 293 cells transfected with a plasmid expressing the foxp3 gene, kindly provided by Dr Oukka and previously described (Betelli et al, Proc Natl Acad Sci USA. 2005 102:5138-43) and to a culture of 293 cells transfected with a control plasmid together with a plasmid expressing luciferase under a promoter inducible by NF-κB (Ref 631904, pNF-kB-Luc, Clontech) has been studied. The 293 cells were transfected by means of using lipofectamine with plasmid pNF-kB-Luc expressing luciferase under a promotor inducible by transcription factor NF-kB, in the presence or absence of plasmid pcDNA, pcDNA-Foxp3 and peptide P60 (SEQ ID NO: 1) (100 µM). After 24 hours of culture, the cells were harvested and the luciferase activity in the cell extracts was measured by means of using a suitable kit (Promega, Maddison, USA) and the luminometer (Orion Microplate luminometer, Berthold detection systems, Germany). The results obtained are shown in FIG. 9, wherein it can be seen that the presence of scurfin in the cells inhibits the expression of luciferase and that the presence of peptide P60 (SEQ ID NO: 1) restores the expression of luciferase.

EXAMPLE 5

In Vivo Immunoenhancement of Anti-Tumor Vaccines by Means of Administering Scurfin-Inhibiting Peptides In view of the previously obtained results, in vivo assays have been carried out to measure the immunoenhancing effect of the administration of scurfin-inhibiting peptides on antitumor vaccination.

The tumor model used for this assay has been a model based on the CT26 colon cancer line, described in a previous work of the laboratory of the inventors (Casares et al, 2001. Eur J Immunol 31:1780-9; Casares et al., 2003. J Immunol 171:5931-9), since the inventors had previously shown that, in this model, Treg lymphocytes have an immunosuppressive effect favoring tumor growth (Casares et al., 2003, mentioned above).

The synthetic peptide (SEQ ID NO: 8) was used as a vaccine antigen, which peptide contains a cytotoxic T determinant for the CT26 line (Huang, A. Y. et al, Proc Natl Acad Sci USA, 1996. 93:9730-9735) and the immunization of which delays the tumor growth to a certain extent, without eliminating it due to the presence of Treg lymphocytes (Casares et al., 2003, mentioned above).

Briefly, groups of 6 six-week old BALB/c mice (Charles River) were immunized with peptide AH1 (SEQ ID NO: 8) as described in Casares et al., 2001, mentioned above, in the presence or absence of peptide P60 (SEQ ID NO: 1). Ten days after the immunization, the mice were subcutaneously injected with $5 \times 10^5$ CT26 cells, and the tumor evolution was measured.

Figure 10:
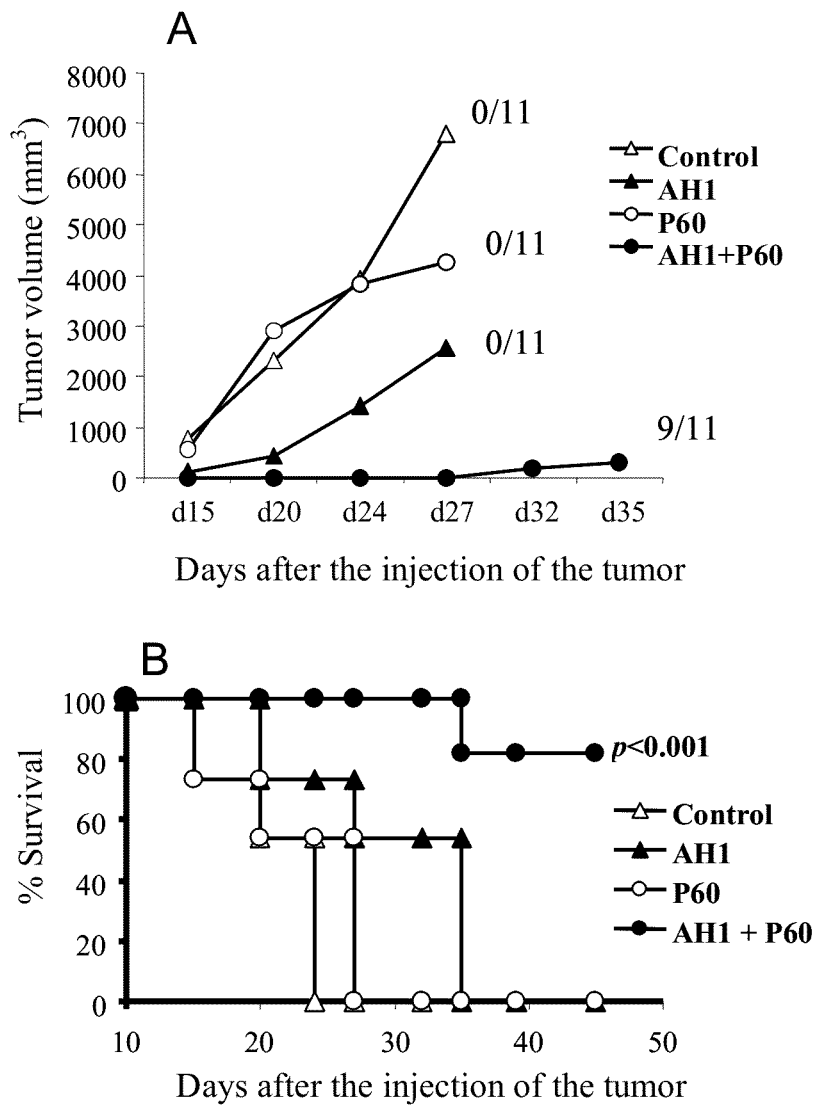
FIG. 10 shows the effect of the administration of peptide P60 (SEQ ID NO: 1) in the enhancement of the antitumor response of the vaccination with the peptide AH1 (SEQ ID NO: 8). Groups of mice BALB/c were immunized with saline (Control group n=11) or with peptide AH1 (SEQ ID NO: 8) emulsified in incomplete Freund's adjuvant (IFA) (n=22) (as described in Casares et al, 2003. J Immunol 171:5931-9). Eleven of the mice immunized with peptide AH1 (SEQ ID NO: 8) were treated with saline during days 0, 2, 4, 6, 8 and 10 after the immunization, whereas the 11 remaining mice were treated with 50 nm/mouse of peptide P60 (SEQ ID NO: 1) dissolved in saline and administered intraperitoneally (i.p.). Another control group (n=11) of non-immunized mice was introduced, which mice were only treated with peptide P60 (SEQ ID NO: 1) in phosphate buffered saline (PBS) following the same treatment regimen as the previous group.

As shown in FIG. 10, the administration of said peptide P60 (SEQ ID NO: 1) during the days after the immunization with peptide AH1 protected the mice from the onset of the tumor. In fact, only 2 of the 11 mice immunized with peptide AH1 and treated with peptide P60 (SEQ ID NO: 1) developed a palpable tumor (82% protection), whereas the protection in the remaining groups was significantly lower, developing lethal tumors (mice immunized with AH1 alone (0%), with peptide P60 (SEQ ID NO: 1) alone (10%) or with PBS alone (0%)) (n=11 in all the cases).

FIG. 10A shows the tumor growth curves whereas FIG. 10B shows the survival curves of the different experimental groups (Kaplan-Meier Representation). p<0.001 indicates the result of the statistical analysis by means of the log-rank test.

The invention claimed is:

1. An isolated peptide with capacity to bind to scurfin, selected from the group consisting of: a peptide set forth in SEQ ID NO: 1, SEQ ID NO: 2, SEQ ID NO: 3, SEQ ID NO: 18, and SEQ ID NO: 19; and pharmaceutically acceptable salts thereof.

2. The peptide according to claim 1, further having the capacity to inhibit the biological activity of scurfin in vitro and/or in vivo.

3. The peptide according to claim 1, consisting of the amino acid sequence of SEQ ID NO: 18.

4. The peptide according to claim 1, consisting of the amino acid sequence of SEQ ID NO: 1.

5. The peptide according to claim 1, consisting of the amino acid sequence of SEQ ID NO: 19.

6. The peptide according to claim 1, consisting of the amino acid sequence of SEQ ID NO: 3.

7. The peptide according to claim 1, selected from the group consisting of SEQ ID NO: 1, SEQ ID NO: 2 and SEQ ID NO: 3, and its pharmaceutically acceptable salts.

8. A fusion protein comprising:
(i) a peptide according to claim 1; and
(ii) a carrier peptide with capacity to internalize a peptide in a cell.

9. The fusion protein according to claim 8, wherein said carrier peptide comprises an amino acid sequence selected from the group consisting of SEQ ID NO: 9, SEQ ID NO: 10, SEQ ID NO: 11, SEQ ID NO: 12, SEQ ID NO: 13, and SEQ ID NO: 14.

10. The fusion protein according to claim 9, further comprising a spacer peptide located between said peptide [peptide (i)] and said carrier peptide [peptide (ii)].

11. The fusion protein according to claim 9, further comprising an amino acid sequence useful for the isolation or purification of the fusion protein of the invention.

12. A pharmaceutical composition comprising a therapeutically effective amount of a peptide according to claim 1 together with at least one pharmaceutically acceptable excipient.

13. The pharmaceutical composition according to claim 12, further comprising, one or more compounds inhibiting or regulating the immunosuppressive activity of different Treg lymphocytes.

14. A method for treating a neoplastic disease or an infectious disease in a subject in need thereof which comprises administering to said subject a therapeutically effective amount of a peptide according to claim 1, wherein said neoplastic disease is selected from the group consisting of colon cancer and hepatocarcinoma; and wherein said infectious disease is a disease caused by hepatitis C virus.

15. The method according to claim 14, wherein the peptide consists of the amino acid sequence of SEQ ID NO: 1.

16. The method according to claim 14, wherein said neoplastic disease is colon cancer.

* * * * *

SEQUENCE LISTING

```
<160> NUMBER OF SEQ ID NOS: 19

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct

<400> SEQUENCE: 1

Arg Asp Phe Gln Ser Phe Arg Lys Met Trp Pro Phe Phe Ala Met
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Arg Asp Phe Gln Ser Phe Arg Lys Met Trp Pro Phe Phe
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Arg Asp Phe Gln Ser Phe Arg Lys Met Trp Pro Phe Phe Ala
1               5                   10
```

```
<210> SEQ ID NO 4
<211> LENGTH: 14
<212> TYPE: PRT
<213> ORGANISM: Artificial Sequence
<220> FEATURE:
<223> OTHER INFORMATION: Synthetic Construct

<400> SEQUENCE: 4

Asp Phe Gln Ser Phe Arg Lys Met Trp Pro Phe Phe Ala Met
1               5                   10

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
tgaattttct gtatgagg                                                 18

<210> SEQ ID NO 6
<211> LENGTH: 15
<212> TYPE: PRT
<213> ORGANISM: Homo sapiens
<220> FEATURE:
<221> NAME/KEY: source
<222> LOCATION: (1)..(15)
<223> OTHER INFORMATION: Peptide corresponding to amino acids 123-137 of
      the human CD81

<400> SEQUENCE: 6

Val Lys Gln Phe Tyr Asp Gln Ala Leu Gln Gln Ala Val Val Asp
1               5                   10                  15

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Ser Ile Ile Asn Phe Glu Lys Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Ser Pro Ser Tyr Val Tyr His Gln Phe
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Construct

<400> SEQUENCE: 9

Arg Lys Lys Arg Arg Gln Arg Arg Arg
1               5
```

```
<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Tyr Gly Arg Lys Lys Arg Arg Gln Arg Arg Arg
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Cys Gly Ile Ser Tyr Gly Arg Lys Lys Arg Arg Gln Arg Arg Arg
1               5                   10                  15

<210> SEQ ID NO 12
<211> LENGTH: 16
<212> TYPE: PRT
<213> ORGANISM: Drosophila antennapedia
<220> FEATURE:
<221> NAME/KEY: source
<222> LOCATION: (1)..(16)
<223> OTHER INFORMATION: Peptide derived from the D. antennapedia Antp
      protein, comprising moieties 43-58 of said Antp protein

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct

<400> SEQUENCE: 13

Lys Phe Val Arg Ser Arg Arg Pro Arg Thr Ala Ser Cys Ala Leu Ala
1               5                   10                  15

Phe Val Asn

<210> SEQ ID NO 14
<211> LENGTH: 8
<212> TYPE: PRT
<213> ORGANISM: Artificial Sequence
<220> FEATURE:
<223> OTHER INFORMATION: Synthetic Construct

<400> SEQUENCE: 14

Ser Cys Ala Leu Ala Phe Val Asn
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Tyr Thr Asp Ile Glu Met Asn Arg Leu Gly Lys
```

```
<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Ala His Gly His Arg Pro
1               5

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct

<400> SEQUENCE: 17

Pro Ile His Asp His Asp His Pro His Leu Val Ile His Ser
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(15)
<223> OTHER INFORMATION: Xaa can be any amino acid

<400> SEQUENCE: 18

Arg Asp Phe Gln Ser Phe Arg Lys Met Trp Pro Phe Phe Xaa Xaa
1               5                   10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa can be any amino acid

<400> SEQUENCE: 19

Arg Asp Phe Gln Ser Phe Arg Lys Met Trp Pro Phe Phe Xaa
1               5                   10
```